United States Patent
Devaux et al.

(10) Patent No.: US 7,482,000 B2
(45) Date of Patent: Jan. 27, 2009

(54) MUTANT FAB FRAGMENTS OF THE CHIMERIC 13B8.2 ANTI-CD4 ANTIBODY AND THEIR APPLICATIONS

(75) Inventors: Christian Devaux, Montpellier (FR); Cédric Bes, Montpellier (FR); Laurence Briant-Longuet, Gallargues (FR); Martine Cerutti, Saint-Christol-les-Alès (FR); Gérard Devauchelle, Saint-Christol-les-Alès (FR); Thierry Chardes, Assas (FR); Claude Granier, Clapiers (FR); Bernard Pau, Montpellier (FR)

(73) Assignee: Centre National de la Recherche Scientifique - CNRS (FR)

( * ) Notice: Subject to any disclaimer, the term of this patent is extended or adjusted under 35 U.S.C. 154(b) by 0 days.

(21) Appl. No.: 11/029,574

(22) Filed: Jan. 5, 2005

(65) Prior Publication Data

US 2005/0226874 A1    Oct. 13, 2005

Related U.S. Application Data

(63) Continuation of application No. PCT/FR03/02108, filed on Jul. 7, 2003.

(30) Foreign Application Priority Data

Jul. 5, 2002    (FR) .................................. 02 08486

(51) Int. Cl.
    A61K 39/395    (2006.01)
(52) U.S. Cl. ................................. 424/133.1; 424/144.1
(58) Field of Classification Search ........................ None
    See application file for complete search history.

(56) References Cited

U.S. PATENT DOCUMENTS

| 5,728,821 | A  | * | 3/1998 | Yelton et al. ............. 536/23.53 |
| 6,241,986 | B1 | * | 6/2001 | Zolla-Pazner et al. .... 424/142.1 |
| 2002/0099179 | A1 | * | 7/2002 | Jolliffe et al. ............ 530/387.3 |

OTHER PUBLICATIONS

Bes et.al. Mapping the paratoe of anti-CD4 recombinant Fab 13B8.2 by combining parallel peptide synthesis and site directed mutagenesis. The J. Biol. Chem., 2003; 278: 14265-14273.*
Tisch et. al. Antigen-specific immunotherapy: is it real possibility to combat T-cell-mediated autoimmunity. PNAS, 1994; 91: 437-438.*
Cosimi et al. (Surgery. Aug. 1990;108(2):406-13.*
Gottlieb et al. (Am Acad Dermatol. Oct. 2000;43(4):595-604.*
Choy et al., Br J Rheumatol. May 1998;37(5):484-90.*
Rudikoff et al, Proc. Natl. Acad. Sci. USA, 79: 1979-1 983, Mar. 1982.*
Colman P. M., Research in Immunology, 145:33-36, 1994.*
Chien et al., Proc Natl Acad Sci U S A. Jul. 1989;86(14):5532-6.*

Cédric Bès et al., *The chimeric mouse-human anti-CD4 Fab 13B8.2 expressed in baculovirus inhibits both antigen presentation and HIV-1 promoter activation*, Human Antibodies, vol. 10, No. 2, 2001, pp. 67-76.
Cédric Bès et al., *Efficient CD4 binding and immunosuppressive properties of the 13B8.2 monoclonal antibody are displayed by its CDR-HI-derived peptide CB1¹*, FEBS Letters, Elsevier Science Publishers, vol. 508, No. 1, Nov. 9, 2001, pp. 67-74.
Cédric Bèet al., *Mapping the Paratope of Anti-CD4 Recombinant Fab 13B8.2 by Combining Parallel Peptide Synthesis and Site-directed Mutagenesis*, The Journal of Biological Chemistry, vol. 278, No. 16, Apr. 18, 2003, pp 14265-14273.
Florence Casset et al., *A peptide mimetic of an anti-CD4 monoclonal antibody by rational design*, Biochemical and Biophysaical Research Communications, vol. 307, No. 1, Jul. 18, 2003, pp. 198-205.
Chardes et al., *Efficient amplification and directed sequencing of mouse variable regions from any immunoglobulin gene family*, FEBS Letters 452 (1999) 386-394.
Benkirane et al., *An antibody that binds the immunoglobulin CDR3-like region of the CD4 molecule inhibits provirus transcription in IIIV-infected T cells*; The EMBO Journal, vol. 12, No. 13, pp. 4909-4921, 1993.
Dhiver, et al.; Abstract of *Pilot phase I study using zidovudine in association with a 10-day course of anti-CD4 monoclonal antibody in seven AIDS patients*; PubMed No. 2576628, 1989.
Benkirane, M. et al., "An Ambody that Binds the Immunoglobulin CDR3-Like Region of the CD4 Molecule Inhibits Provirus Transcription in HIV-infected T Cells," *The Embo Journal*, 1993, vol. 12, No. 13, pp. 4909-4921.
Benkiran, M. et al., "Functional Epitope Analysis of the Human CD4 Molecule; Antibodies That Inhibit Human Immunodeficiency Virus Type 1 Gene Expression Bind to the Immunoglobulin CDR3-Like Region of CD4," *Journal of Virology*, Nov. 1995, vol. 69, No. 11, pp. 6898-6903.
Briant, L. et al., "Bioactive CD4 Ligands as Pre- and/or Postbinding Inhibitors of HIV-1," *Advances in Pharmacology*, 2000, vol. 48, pp. 373-407.
Briant, L. et al., The Protein Tyrosine Kinase *p56* Is Required for Triggering NF-kB Activation upon Interaction of Human Immunodeficiency Virus Type 1 Envelope Glycoprotein gp120 with Cell Surface CD4, *Journal of Virology*, Jul. 1998, vol. 72, No. 7, pp. 6207-6214.
Chardes, T. et al., "Efficient Amplification and Direct Sequencing of Mouse Variable Regions from any Immunoglobulin Gene Family," *FEBS Letters*, 1999, vol. 452, pp. 386-394.
Cohen, G. H. et al., "Refined Structure of the Monoclonal Antibody HyHEL-5 with Its Antigen Hen Egg-White Lysozyme," *Acta Crystallographics*, 1996, vol. D 52, pp. 315-326.
Corbeau, P. et al., "Jg CDR3-Like Region of the CD4 Molecule is Involved in HIV-Induced Syncytia Formation but not in Viral Entry," *The Journal of Immunology*, Jan. 1, 1993, vol. 150, pp. 290-301.

(Continued)

*Primary Examiner*—Eileen B. O'Hara
*Assistant Examiner*—Zachary Skelding
(74) *Attorney, Agent, or Firm*—DLA Piper LLP (US)

(57) ABSTRACT

A mutant Fab fragment of the 13B8.2 anti-CD4 antibody that binds a CD4 molecule and includes a mutation of at least one residue in a position situated in the VH variable domain of the heavy chain and/or in a position situated in the Vκ variable domain of the light chain.

13 Claims, 8 Drawing Sheets

OTHER PUBLICATIONS

Deckert, P. M. et al., "CD4-Imitating Antibodies in HIV Infection and Anti-Idiotypic Vaccination," *The Journal of Immunology*, 1996, vol. 156, pp. 826-833.

Dhiver, C. et al., "Pilot Phase I Study Using Zidovudine in Association with a 10-Day Course of Anti-CD4 Monoclonal Antibody in Seven AIDS Patients," *Aids* 1989, vol. 3, pp. 835-842.

Fishwild, D. M. et al., "High-Avidity Human IgG kappa Monoclonal Antibodies from a Novel Strain of Minilocus Transgenic Mice," *Nature Biotechnology*, Jul. 1996, vol. 14, pp. 845-851.

Foote, J et al., "Antibody Framework Residues Affecting the Conformation of the Hypervariable Loops," *J.Mol. Biol.*, 1992, vol. 224, pp. 487-499.

Frank, R., "Spot-Synthesis: An Easy Technique for the Positionally Addressable, Parallal Chemical Synthesis on a Membrane Support," *Tetrahedron*, 1992, vol. 48, No. 42, pp. 9217-9232.

Gorman, S. D. et al., "Reshaping a Therapeutic CD4 Antibody," *Proc. Natl. Acad. Sci. USA*, May 1991, vol. 88, pp. 4191-4185.

Ho, S. N. et al., "Site-Directed Mutagenesis by Overlap Extension Using the Polymerase Chain Reaction" *Gene*, 1989, vol. 77, pp. 51-59.

Karlsson, R. et al., "Kinetic and Concentration Analysis Using BIA Technology," *Companion Methods Enzymology*, 1994, vol. 6, pp. 99-110.

Laune, D. et al., "Application of the Spot Method to the Identification of Peptides and Amino Acids from the Antibody Paratope that Contribute to Antigen Binding," *Journal of Immunology Methods*, 2002, vol. 267, pp. 53-70.

Laune, D et al., "Peptide Models of Immunological Recognition: Paratope Dissection by Multiple Peptide Synthesis," *Clin. Chem. Lab. Med.*, 1998, vol. 36, No. 6, pp. 367-371.

Laune, D. et al., "Systematic Exploration of the Antigen Binding Activity of Synthetic Peptides Isolated from the Variable Regions of Immunoglobulins," *The Journal of Biological Chemistry*, 1997, vol. 272, No. 49, pp. 30937-30944.

Maddon, P.J. et al., "Structure and Expression of the Human and Mouse T4 Genes," *Proc Natl. Acad. Sci. USA*, 1987, vol. 84, pp. 9155-9159.

Manca, F. et al., "Antigenicity of HIV-Derived T Helper Determinants in the Context of Carrier Recombinant Proteins Effect on T Helper Cell Repertoire Selection," *Eur. J. Immunol.*, 1996, vol. 26, pp. 2461-2469.

Monnet, C. et al., "Synthetic Peptides Derived from the Variable Regions of an Anti-CD4 Monoclonal Antibody Bind to CD4 and Inhibit HIV-1 Promoter Activation in Virus-infected Cells," *The Journal of Biological Chemistry*, 1999, vol. 274, No. 6, pp. 3789-3796.

Poul, M-A. et al., "Design of Cassette Baculovirus Vectors for the Production of Therapeutic Antibodies in Insect Cells," *Immunotechnology*, 1995, pp. 189-196.

Poulin, L. et al., "Several CD4 Domains Can Play a Role in Human Immunodeficiency Virus Infection of Cells," *The Journal of Virology*, Sep. 1991, vol. 65, pp. 4893-4901.

Proba, K. et al., "A Natural Antibody Missing a Cysteine in $V_H$: Consequences for Thermodynamic Stability and Folding," J. Mol. Biol., 1997, vol. 265, pp. 161-172.

Pulito, V. L. et al., "Humanization and Molecular Modeling of the Anti-CD4 Monoclonal Antibody, OKT4A," *The Journal of Immunology*, 1996, vol. 156, pp. 2840-2850.

Reimann, K.A. et al., "A Humanized form of a CD4-Specific Monoclonal Antibody Exhibits Decreased Antigenicity and Prolonged Plasma Half-Life in Rhesus Monkeys while Retaining Its Unique Biological and Antiviral Properties," *Aids Res. Hum. Retr.*, 1997, vol. 13, pp. 933-943.

Sattentau, Q. J. et al., "Structural Analysis of the Human Immunodeficiency Virus-Binding Domain of CD4," *J. Exp Med.* Oct. 1989, vol. 170, pp. 1319-1334.

Schedel, I. et al., "Phase II Study of Anti-CD4 Idiotype Vaccination in HIV Positive Volunteers," *Vaccine*, 1999, vol. 17, pp. 1837-1845.

Taniyama, Y. et al., "Secretion in Yeast of Mutant Human Lysozymes with and without Glutathionen Bound to Cysteine 95," *Journal of Biological Chemistry*, Oct. 5, 1990, vol. 265, No. 28, pp. 16767-16771.

Vrana, M. et al., "Purification of Homogenous Murine Immunoglobulins with Anti-Fructofuranan Specificity," *The Journal of Immunology*, Jun. 1976, vol. 116, pp. 1662-1664.

* cited by examiner

A

B

Purification of the bands
Estimation of the quantities
Overlap PCR:

MUTANT FAB FRAGMENTS OF THE CHIMERIC 13B8.2 ANTI-CD4 ANTIBODY AND THEIR APPLICATIONS

RELATED APPLICATION

This is a continuation of International Application No. PCT/FR2003/002108, with an international filing date of Jul. 7, 2003 (WO 2004/005350, published Jan. 15, 2004), which is based on French Patent Application No. 02/08486, filed Jul. 5, 2002.

FIELD OF THE INVENTION

This invention pertains to the field of immunotherapy. In particular, it pertains to new ligands for the CD4 molecule, mutant Fab fragments of the 13B8.2 anti-CD4 antibody. The invention also pertains to pharmaceutical compositions containing these ligands for the treatment of pathologies in which the CD4 molecule is implicated.

BACKGROUND

Since the identification of the CD4 molecule by the W3/25 antibody and the demonstration for this antibody of a biological effect of immunosuppression, the anti-CD4 antibodies have attracted noteworthy clinical interest. They have been targets of extensive attention on the part of the pharmaceutical industry, for which they represent a market of tens of millions of individuals grouping together pathologies as varied as the autoimmune disorders, graft rejection and HIV infection.

There exist at present around one hundred anti-CD4 antibodies, most of which have been reported to have an immunosuppressive activity. However, the majority of these antibodies are only used as immunologic reagents (ELISA, flow cytometry, diagnostics, etc.). Around ten of the antibodies have been developed for therapeutic use but, at present, only five anti-CD4 antibodies are effectively in the process of clinical trials: 1) The OKT4a antibody: of murine origin, the OKT4a antibody recognizes at the surface of the human CD4 molecule an epitope overlapping the CDR2-like region of the D1 domain. 2) CLENOLIXIMAB™: this anti CDR2-like antibody of the D1 domain of CD4 was characterized and studied under the name of KELIXIMAB™ and improved by Newman et al. by mutation to have not only a capacity to bind the Fc receptor diminished by a factor of 1000, but also a half-life improved from four to nine days. 3) The Hu5A8 antibody: this is an IgG4/κ anti-domain D2 of CD4 of murine origin humanized by the method of CDR-grafting (Boon et al., 2002). It is claimed that this antibody has a strong anti-HIV activity (Burkly et al., 1992; Moore et al., 1992; Reimann et al., 1997). Its non-immunosuppressive nature and the lack of harmful effect on the level of circulating T CD4+ lymphocytes (Reimann et al. 1997) make it an excellent candidate in the framework of the treatment of AIDS in combination or in those patients who are refractory to the currently available therapies. 4) The MDX-CD4 antibody: this anti-domain D1 of CD4 is totally human and did not require any engineering (Fishwild et al., 1996). Isolated from a murine hybridoma after immunization of transgenic mice, it is presently used in a form re-expressed in CHO cells which has no effect on its specificity, its affinity for the CD4 molecule nor its functional characteristics (Fishwild et al., 1999). 5) The CAMPATH-9H antibody which is an IgG1/κ humanized by the CDR-grafting method based on a rat antibody (Gorman et al., 1991). Obtained by immunization of rats, this anti-domain D1 antibody of CD4 was initially described as improving the quality of the treatment of an autoimmune disorder by another antibody, CAMPATH-1H itself directed against the CD52 molecule. A new engineering approach was able to produce this antibody in myeloma cells of non-secretor NSO mice and not induce the mechanism of complement dependent cytotoxicity (CDC) and only slightly the mechanisms of antibody dependent cellular cytotoxicity (ADCC) (Peakman et al., 1994).

Lastly, the 13B8.2 monoclonal antibody (IOT4a) was described at the end of the 1980's as an antiviral agent preventing the proliferation of HIV. These data immediately led to Phase I clinical testing in a trial involving seven AIDS patients (Dhiver et al., 1989). Many other clinical trials were carried out with this 13B8.2 antibody (Schedel et al., 1993; Deckert et al., 1996; Schedel et al., 1999). All of these studies confirmed the clinical benefit of the administration of the antibody on the progression of the disease. The studies carried out by the group of C. Devaux resulted in the determination of the mechanism of action of the 13B8.2 antibody (for review, Briant and Devaux, 2000).

There was demonstrated the existence of an association between its antiviral activity and an inhibition of the proliferation of HIV resulting from the inactivation of the cascades of intracellular signalizations normally enabling the induction of the expression of the viral genome.

That antiviral activity could be the consequence of many factors such as the induction of a negative signal not dependent on $p56^{lck}$ nor on the HIV co-receptors or the inhibition of a functional mechanism implicating the dimerization oligomerization of the CD4 molecule. In both cases, the 13B8.2 antibody inhibits the signalization cascades implicating the pathway of the MAPkinases, pathways that normally lead to the nuclear translocation of the NF-κB transcription factor.

The 13B8.2 monoclonal antibody was described as directed against the CDR3-like loop of the D1 domain of the CD4 molecule (Sattentau et al., 1989; Corbeau et al., 1993; Houlgatte et al., 1994).

The first clinical trials undertaken with the 13B8.2 antibody were predictive of the therapeutic potential of that molecule. Nevertheless, its development into a product of pharmaceutical interest encountered numerous problems inherent in the structure and the murine origin of the antibody. In fact, the first clinical trials involving AIDS patients and incorporating the 13B8.2 antibody in its original murine version revealed the induction of a HAMA response which, although relatively mild, still interfered with the therapeutic efficacy of the molecule (Dhiver et al., 1989; Deckert et al., 1996; Schedel et al., 1999).

In order to limit the immunogenicity of that molecule and to develop a product of therapeutic interest, a recombinant chimeric Fab fragment of the 13B8.2 antibody was developed and prepared after isolation and sequencing of the domains V of the 13B8.2 antibody (Chardès et al., 1999) by expression by the baculovirus/insect cell system for presenting the domains V of the heavy and light chains of the parental murine antibody fused respectively with the human $CH_1$-γ1 and Cκ domains.

It has been shown that the recombinant chimeric Fab fragment of the 13B8.2 anti-CD4 antibody is capable of binding CD4 with the same epitopic specificity as the parental antibody. Furthermore, this fragment reproduces the biological properties of the 13B8.2 antibody from (1) an antiviral point of view, inhibition of the activation of the HIV promoter and reverse-transcriptase activity and (2) from an immunosuppression point of view, inhibition of the cellular activation subsequent to the presentation of antigens and mixed lymphocyte reactions.

That functionality has already been demonstrated for the chimeric Fab fragment of the antibody (Benkirane et al., 1995). Chimerization thus does not affect its capacity to inhibit, viral proliferation even if a relatively lesser efficacy is noted.

The evaluation of the biological properties of the recombinant Fab fragment shows that this Fab fragment exhibits an activity similar to that of the parental antibody both in terms of inhibition of the activation of the HIV promoter and in the capacity to inhibit the secretion of IL-2 of a T CD4$^+$ lymphocyte in response to the presentation of antigen. (The chimeric mouse-human anti-CD4 Fab 13B8.2 expressed in baculovirus inhibits both antigen presentation and HIV-1 promoter activation. (Bès C. et al. Human Antibodies 10 (2001) 67-76).

The recombinant chimeric Fab fragment of the 13B8.2 antibody possesses the double advantage of being of smaller size than a complete antibody, which improves its pharmacodynamics constants and enables it in a sense to escape the immune system, but also to exhibit good immunosuppressive qualities, which would explain the absence of HAMA type response noted during the preliminary clinical phases with the complete antibody in its murine form.

SUMMARY OF THE INVENTION

This invention relates to a mutant Fab fragment of 13B8.2 anti-CD4 antibody that binds a CD4 molecule and includes a mutation of at least one residue in a position situated in the VH variable domain of the heavy chain and/or in a position situated in the Vκ variable domain of the light chain.

This invention also relates to a pharmaceutical composition including a therapeutically effective amount of a mutant Fab fragment and an excipient.

This invention further relates to a method for preventing or treating immunological intolerance reactions including administering a therapeutically effective amount of the pharmaceutical composition to a mammal.

This invention also further relates to a method for preventing or treating graft versus host type reactions including administering a therapeutically effective amount of the pharmaceutical composition to a mammal.

This invention still further relates to a method for preventing or treating cancers involving the CD4 molecule including administering a therapeutically effective amount of the pharmaceutical composition to a mammal.

This invention yet again relates to a method for preventing or treating an immunodeficiency linked to a viral infection including administering a therapeutically effective amount of the pharmaceutical composition to a mammal.

BRIEF DESCRIPTION OF THE DRAWINGS

FIG. 1A illustrates the scanning of a membrane with a CD4 probe corresponding to peptide 1 GVIWRS (SEQ ID NO: 62) and to peptide 2 WRSGIT (SEQ ID NO: 63) covering the residues 49-57 of the region CDR-H2 according to the numeration of Kabat and their respective sets of hexapeptide analogues with alanine.

FIG. 1B illustrates the quantitative analysis of the Spot reactivities of peptides 1 and 2 and their respective alanine analogues covering the residues 49-57 of the CDR-H2 region. Each bar represents the reactivity of a hexapeptide the sequence of which comprises an Ala residue in place of the indicated amino acid.

FIG. 1C shows the Spot contributor residues of each of the CDR regions of the variable regions of heavy and light chains, measured as percentage of inhibition of the binding to the CD4 molecule (vertical bar). The identification of the CDR performed according to Kabat (outlined boxes) and IMGT (shadowed boxes) is indicated. VH CDR1 Region is disclosed as SEQ ID NO: 83; VL CDR1 Region is disclosed as SEQ ID NO.: 84; VH CDR2 Region is disclosed as SEQ ID NO: 85; VH CDR3 Region is disclosed as SEQ ID NO: 86; VL CDR3 Region is disclosed as SEQ ID NO.: 87.

FIG. 2A illustrates the ELISA analysis of the mutants Y36-L, C88-L, F32H, H35-H, W52-H and R53-H in relation to a standard immunoglobulin curve.

FIG. 2B shows the Western blot analysis of the 50-kDa band of said Fab fragments developed with an anti-kappa chain antibody conjugated to peroxidase.

FIG. 5A shows the dose-response percentage of the inhibition of the secretion of 112 at different concentrations of the wild Fab in relation to the IC10 control Fab.

FIG. 5B shows the percentage of inhibition of the secretion of 112 by each of the mutant recombinant Fab fragments (nd=not determined). The mean of the absorbances at 450 nm ranged from 0.015 for the pdb 10F cells co-cultured with the non-stimulated EBV-Lu presenting cells to 1.28 for the pdb 10F cells co-cultured with the presenting cells of EBV-Lu antibodies stimulated with the peptide pep24. The positive control for the secretion of 112 by incubation of the murine anti-CD3 antibody (PHARMINGEN™, San Diego, Calif.) with the T pdb 10F cells produced an absorbance of 2.30.

FIG. 6A shows the inhibition of expression of the gene of beta-galactosidase in HeLa P4 cells infected by the virus HIV-1$_{Lai}$ cultured in the presence of different concentrations of wild recombinant Fab.

FIG. 6B shows the inhibition of the expression of the gene of beta-galactosidase for each of the mutant recombinant Fab fragments H91-L, F32-H, H35-H, W52-H and R53—H. The mean absorbance at 410 nm ranged from 0.01 for the non-infected indicator cells to 0.40 for the indicator cells infected by the virus HIV-1$_{Lai}$.

The SCR residues binding CD4, as confirmed by directed mutagenesis, are identified in dark gray whereas the residues not implicated in the binding to CD4 as defined by mutagenesis are shown in light gray. This figure was obtained with the Swiss pdb Viewer visualization software program.

Figure 8:
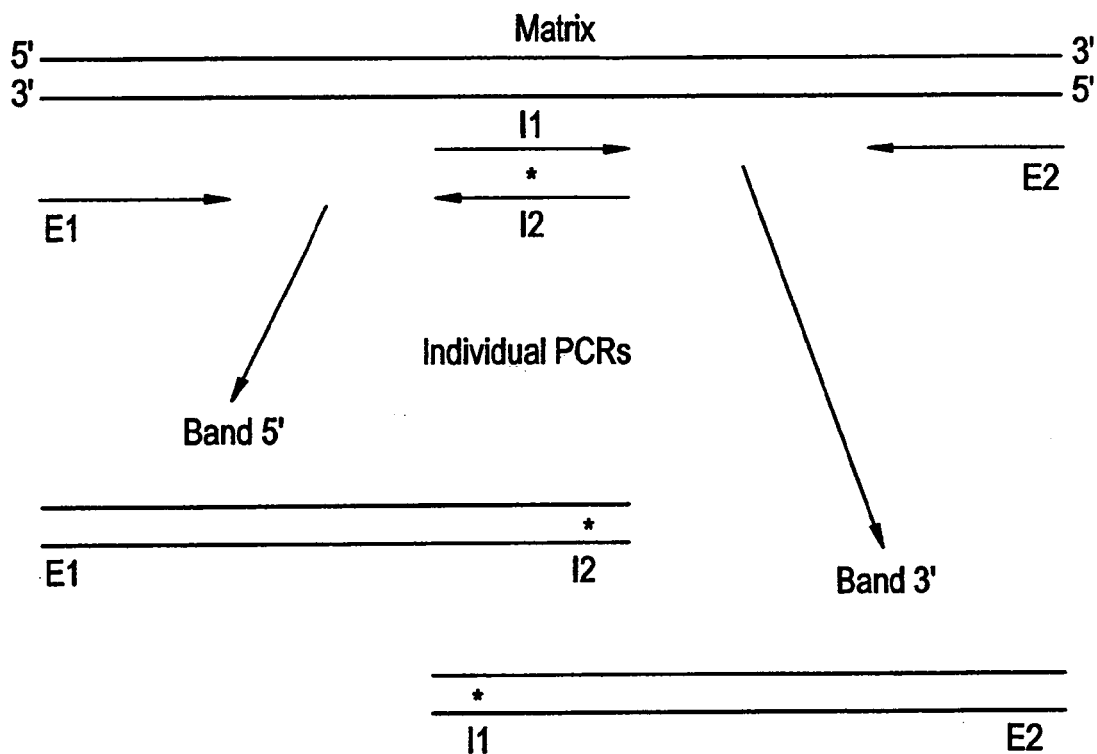
Figure 8:
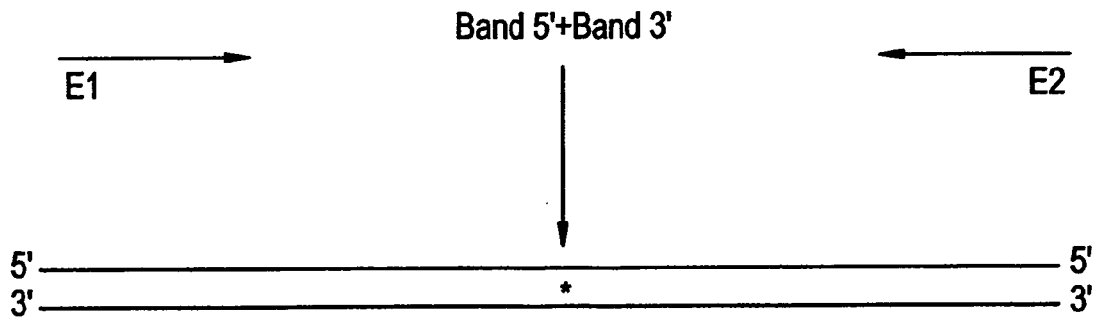

FIG. 8 shows a diagram of the method used for amplifying the sequences coding the variable domains of the heavy and light chains of the mutant Fab fragments of the 13B8.2 antibody. These sequences were obtained by overlapping PCR.

DETAILED DESCRIPTION

We were able to identify critical residues of the paratope of the 13B8.2 antibody implicated in binding to the CD4 molecule, which represents progress in the development of new generation anti-CD4 molecules. Such a study of a paratope of an antibody is performed using the peptides overlapping the variable regions of the Fab fragment with a labeled antigen. This approach is unusual because it is commonly accepted that in order for an antibody to recognize the antigen against which it is directed, the three-dimensional structure of its paratope must be conserved.

We applied this approach to the variable regions of the Fab fragment of the 13B8.2 chimeric antibody. We were thereby able to identify mutations which improve the biological properties of the fragments, whether or not these mutations affect the critical residues in the antibody/ligand interaction of the second generation recombinant chimeric Fab fragments of the 0.13B8.2 antibody.

Our research confirmed the results of such an approach. In fact, the experimental results obtained by the directed mutagenesis techniques prove that the Spot method of parallel multisynthesis of peptides on cellulose support (Frank R, Tetrahedron, 1992, 48: 9217-9232) applied to the paratope of the 13B8.2 antibody enables identification of the critical residues implicated in the biological activity of the antibody.

On the one hand, the production of molecules derived from a more active antibody is of clinical interest in terms of minimization of the doses to administer thereby providing not only the clinician, but especially the patient with greater comfort.

On the other hand, the complementarity of these diverse Fab molecules is of clinical interest in the case of therapeutic escape in relation to one of them.

We thus developed new mutant Fab fragments derived from the humanized 13B8.2 chimeric monoclonal antibody having immunosuppressive properties.

Based on the 13B8.2 murine hybridoma, the genes coding for the heavy and light chains of the 13B8.2 antibody were amplified by a polymerization chain reaction (PCR) using sets of oligonucleotides hybridizing with each other in the signal sequences of the immunoglobulins (Chardès et al., FEBS Lett 452: 386-394, 1999).

Cloning the variable regions of the 13B8.2 antibody which use the genes VH2-DQ-52-JH3 and Vk12/131-Jk2 was implemented in a first step, then the complete sequences of the VH and Vκ regions of the 13B8.2 antibody were realized.

A humanized Fab fragment of the humanized 13B8.2 anti-CD4 antibody having variable regions cloned from the 13B8.2 murine hybridoma and constant regions of human immunoglobulins was then obtained by molecular genetics in a baculovirus expression system (Cérutti M et al., Protéine Performance, 1995, patent application no. FR 95/00110; INRA/CNRS, 1997 WO 95/20672; Poul M-A et al., Immunotechnology, 1995, 1: 189-196).

Based on the Alascan SPOT data obtained by replacement of an amino acid in a given position in the sequence of a peptide capable of binding the CD4 molecule by the amino acid alanine, we were able to determine which are the residues of the Fab fragment of the 13B8.2 antibody having a particularly important contribution for their binding to the CD4 molecule.

On the basis of the Alascan results, a series of 16 mutant Fab fragments of the humanized 13B8.2 anti-CD4 antibody was produced. 16 residues stemming from the hypervariable CDR1/CDR2/CDR3-VH regions of the variable region of the heavy chain and the CDR1/CDR2-Vκ regions of the variable region of the light chain of the 13B8.2 antibody were successively mutated by an alanine to evaluate the nature of the contributing residues for binding to the CD4 molecule.

The mutant Fab fragments were produced in the baculovirus/insect cell system (Cèrutti M. et al., 1995 patent, Protèine Performance no. FR 95/00110 INRA/CNRS, 1997 WO 95/20672 Poul M-A et al., Immunotechnology, 1995, 1: 189-196). The quality of the mutants was evaluated by ELISA and Western blot. It was found that eight residues (H35, W52, R53, F100κ, W103 of VH and Y32, Y36 and H91 of Vκ) were strong contributors given that a loss of binding to the CD4 molecule of the mutant Fab fragments was observed by the ELISA, Tri fluorescence (FACS) or BIACORE™ techniques.

Three residues (R38 of VH, W35 and Y92 of Vκ) were moderate contributors and it was shown that five other residues (F32, W36, C92, Y102 of VH and C88 of Vκ) were not contributors to the binding of the Fab fragment with the CD4 molecule.

The mutant Fab fragments having mutations on the amino acids defined as contributing to binding with the CD4 molecule also have a loss of biological efficacy such as the activity of inhibition of HIV promoter and the activity of inhibition of antigen presentation.

Molecular modeling of the 13B8.2 paratope was implemented and constitutes a comprehension element supplementary to the interaction with the CD4 molecule.

The role of the positively charged R53 residues of VH and especially H35 of VH and H91 of Vκ appears to be fundamental, probably by enabling binding to the homologous region of the CDR3-like of the CD4 molecule. In fact, this region of the CD4 molecule is negatively charged with the amino acids E87 and D88.

This analysis is reinforced by the fact that a pH gradient of 6 to 8, diminishing the positive charge of the histidine amino acids from 50% to 5%, leads to a decrease in binding on the order of 25% in ELISA.

In conclusion, five mutant Fab fragments of the humanized 13B8.2 anti-CD4 antibody conserve the capacity of binding to the CD4 molecule and the immunosuppressive properties of the 13B8.2 parental antibody.

The invention thus relates to a mutant Fab fragment of the 13B8.2 anti-CD4 antibody binding the CD4 molecule and comprising a mutation of at least one residue in a position situated in the VH variable domain of the heavy chain (SEQ ID NO: 1) or in a position situated in the Vκ variable domain of the light chain (SEQ D NO: 2). The mutant. Fab fragments of the 13B8.2 antibody of the invention preferably have a constant affinity for the CD4 molecule at least equal to that of the wild Fab.

The mutant Fab fragment of the 13B8.2 anti-CD4 antibody preferably comprises a mutation of at least one residue in a position situated in the regions 31-41, 49-57, 61-70 or 90-103 of the VH variable domain of the heavy chain or in a position situated in a position in the regions 19-26, 32-40 or 85-96 of the Vκ variable domain of the light chain.

The mutant Fab fragment is more particularly selected from among the group comprising the C88-L mutant Fab fragments the Vκ variable region of which has a mutation of the cysteine residue in position 88 by an alanine and is identified by the sequence SEQ ID No. 1.6; F32-H, the VH variable region of which has a mutation of the phenylalanine residue in position 32 by an alanine residue and is identified by the SEQ ID No. 3; W36-H, the VH variable region of which presents a mutation of the tryptophan residue in position 36 by an alanine residue and is identified by the SEQ ID No. 5; C92-H, the VH variable region of which presents a mutation of the cysteine residue in position 92 by an alanine residue and is identified by the SEQ ID No. 9; and Y102-H, the VH variable region of which presents a mutation of the tyrosine residue in position 102 by an alanine residue and is identified by the SEQ ID No. 11.

The invention pertains to pharmaceutical compositions comprising an active agent in a therapeutically effective dose of at least one of the mutant Fab fragments of the invention, optionally in the presence of a suitable excipient. The mutant Fab fragment can be used at a concentration comprised between about 1 and about 50 mg, preferably between about 5 and about 10 mg.

The mutant Fab fragment may be used at a concentration between about 0.01 mg/kg and about 2 mg/kg, preferably between about 0.1 and about 0.4 mg/kg of weight of the patient to be treated.

The pharmaceutical compositions of the invention are particularly useful for the treatment of autoimmune pathologies, notably rheumatoid arthritis, but also psoriasis and lupus erythematosus.

According to one particular mode of use, the pharmaceutical compositions of the invention can be used in combination with a preparation comprising anti-TNF ligands. The pharmaceutical compositions of the invention are particularly useful for the treatment or prevention of reactions of immunological intolerance. The pharmaceutical compositions of the invention are also useful for treating reactions triggered in a patient subsequent to an organ transplant, for diminishing or even substantially eliminating the reactions of the graft versus host type to improve the tolerance of the graft.

The pharmaceutical compositions of the invention are also useful for treating cancers implicating the CD4 molecule, such as the CD4+ lymphomas or Cesari's lymphoma and treating AIDS, such as the prevention of mother-infant viral transmission as well as in the context of preventive treatment after an accidental contamination.

The mutant Fab fragments of the 13B8.2 chimeric anti-CD4 antibody are particularly suitable for an immunosuppressive therapy and make it possible notably to avoid treatment escape because they do not induce an anti-idiotypic response.

A pharmaceutical composition according to the invention is thus useful for the preparation of a drug intended for the prevention or treatment of immunodeficiencies linked to a viral infection.

The invention is described below by the description of the experimental studies to prepare, purify and identify the mutant Fab fragments of the 13B8.2 antibody, to compare their behavior in relation to their ligand, the CD-4 molecule, compared to that of the wild Fab and to thereby select those presenting the best biological activities.

Material and Method

Reagents, Cell Lines and Vectors

The plasmid pMC7-T4 coding for the totality of the sequence of the cDNA of the CD4 molecule [Maddon, 1987] was used. As described [Bès, 2001a, 2001b], baculoviruses having CD4 inserted were constructed and subsequently used for the production of soluble human recombinant CD4. For the SPOT analyses, human recombinant CD4 (REPLIGEN INC.™, Needham, Mass.) was biotinylated using commercially available reagents (AMERSHAM PHARMACIA BIOTECH™, Cleveland, Ohio) according to the manufacturer's instructions.

The murine hybridoma line which produces the 13B8.2 monoclonal antibody (IgG1/κ) [Dhiver, 1989; Corbeau, 1993] was obtained from D. Olive and C. Mawas (INSERM U119, Marseille, France).

The B EBV-Lu lymphoblastoid line expressing the molecules HLA DR5.6, DRB52, DQ6.7 and A2 and the murine T pdb10F line expressing human CD4 and the peptide pep24 (PAGFAILKCNNKTFNY) (SEQ ID NO: 59) specific of chimeric TCR [Manca, 1996] was obtained from Professor De Berardinis (National Research Council, Naples, Italy).

The indicator cell line HeLa P4 having the LTR β-galactosidase of HIV-1 [Briant, 1998] was obtained from O, Schwartz (Pasteur Institute, Paris, France). The cell line T A2.1/CD4 [Poulin, 1991] expressing wild-type human CD4 was obtained from D. Littman (New York, N.Y.).

Analysis by Spot Alascan for identifying the contributing residues of the immunoreactive sequences of the 13B8.2 antibody versus CD4.

The general protocol for the synthesis of Spot peptides on cellulose membranes used and that described [Monnet, 1999; Laune, 2002].

On the basis of 202 overlapping dodecapeptides the frame of which was displaced by a single residue, corresponding to the sequence of amino acids deduced from the variable regions of the 13B8.2 antibody, the anti-CD4 immunoreactivity was observed in advance [Bès, 2001b] for the peptides including the sequences 31-41, 49-70 and 90-103 of the heavy chain and the sequences 19-26, 32-40 and 85-96 of the light chain (according to Kabat's numeration).

Seventeen hexapeptides covering said immunoreactive sequences and six analogues of each hexapeptide were synthesized by the Spot method.

The antigenic reactivity of the peptides bound to the cellulose membrane was tested with biotinylated CD4 (1 μg/ml) under conditions that led to the production of a blue precipitate for the reactive spots as described in [Bès, 2001b]. The reactivity of the spots was evaluated by scanning the membrane and measuring the intensity of the spots with the NIH software program image 1.61. The spots of the contributor residues (SCR) of the paratope of the 13B8.2 antibody were identified on the basis of an equal to or greater than 50% of the binding capacity for the antigen in relation to that of the unmodified peptide sequence. Construction of recombinant baculovirus producing wild or mutant Fab fragments of the 13B8.2 antibody The general procedures concerning the cloning and sequencing of the variable regions of the 13B8.2 antibody were implemented as described in [Chardès, 1999; Bès, 2001a, 2001b]. The directed mutagenesis of the genes of the heavy and light chains of the 13B8.2 antibody was performed by overlapping PCR [Ho, 1989]. The sixteen positions that were identified as spot contributing residues (SCR) by alanine scanning and two additional residues (T53 of the light chain and V61 of the heavy chain) as control were mutated by one alanine.

Each mutant was verified by sequencing.

For the preparation of the genes of the heavy chains, fragments of the variable region of the linearized heavy chain PstI/SacI were cloned in the cassette of the transfer vector plasmid pBHuFdγ$_1$ which contains preinstalled upstream the first domain of the heavy chain Cγ$_1$ (Fdγ$_1$) enabling the insertion and expression of the heavy chain of the 13B8.2 antibody under the control of the promoter polyhedrin [Poul, 1995; Bès, 2001a].

For the preparation of the genes of the light chains, the fragments of the variable region of the light chain, linearized XhoI/KpnI, were cloned in the cassette of the transfer vector plasmid pBHuCκ which contains preinstalled upstream the gene Cκ [Poul, 1995; Bès, 2001a] enabling the insertion and expression of the light chain of the 13B8.2 antibody under the control of the promoter p10.

A two-step recombination procedure [Poul, 1995; Bès, 2001a] was performed to construct the recombinant baculoviruses expressing the heavy and light chains of the wild and mutant Fab fragments of the 13B8.2 antibody. An irrelevant control Fab, the anti-digoxin Fab IC10, was expressed in a similar manner in the baculovirus/insect cell system. The "13B8.2" primers These primers were used to amplify the coding sequences of the variable domains of the heavy and light chains of the mutant Fab fragments of the 13B8.2 antibody. These sequences were obtained by overlapping PCR (FIG. 8).

The primers p119F and p119R correspond respectively to the primers E1 and E2 in the framework of the amplification of the heavy chain; the primers p116F and p116R correspond respectively to the primers E1 and E2 in the framework of the amplification of the light chain.

The other primers correspond to the primers I1 and I2 according to the nomenclature "chain (H or L)" "mutated position" "1 or 2", e.g., VhF32F and VhF32R correspond respectively to the primers I1 and I2 used for mutating into alanine the residue F32 (Phe32) of the heavy chain.

TABLE I

Primers used for the mutant Fab 13B8.2 constructions

| NAME | SEQUENCE |
|---|---|
| p119R | 5' ATC CGG AAC AAT GTC GCC GG 3' (SEQ ID NO: 19) |
| P119F | 5' CAT CAC TTA CAA CAA GGG GG 3' (SEQ ID NO: 20) |
| p116R | 5' TAT CAG CCC CAG CGT TGC 3' (SEQ ID NO: 21) |
| p116F | 5' CTG CGA GCA GTT GTT TGT 3' (SEQ ID NO: 22) |
| VhF32F | 5' ACT ACC GCT GGT GTA CAC TGG 3' (SEQ ID NO: 23) |
| VhF32R | 5' TAC ACC AGC GGT AGT AAA TG 3' (SEQ ID NO: 24) |
| VhH35F | 5' GGT GTA GCC TGG GTT CGC 3' (SEQ ID NO: 25) |
| VhH35R | 5' AAC CCA GGC TAC ACC AAA GG 3' (SEQ ID NO: 26) |
| VhW36F | 5' GTA CAC GCG GTT CGC CAG TC 3' (SEQ ID NO: 27) |
| VhW36R | 5' GCG AAC CGC GTG TAC ACC AAA GG 3' (SEQ ID NO: 28) |
| VhR38F | 5' TGG GTT GCC CAG TCT CCA GG 3' (SEQ ID NO: 29) |
| VhR38R | 5' TG GAGA CTG GGC AAC CC 3' (SEQ ID NO: 30) |
| VhW52F | 5' GGA GTG ATA GC GAGA GT GG 3' (SEQ ID NO: 31) |
| VhW52R | 5' ACT TCT CGC TAT CAC TCC C 3' (SEQ ID NO: 32) |
| VhR53F | 5' GTG ATA TGG GCA AGT GGA ATC AC 3' (SEQ ID NO: 33) |
| VhR53R | 5' TCC ACT TGC CCA TAT CAC TCC 3' (SEQ ID NO: 34) |
| VhV61F | 5' TAC AAT GC ACCT TTC ATG TCC 3' (SEQ ID NO: 35) |
| VhV61R | 5' GAA AGG TGC ATT GTA GTC TGT G 3' (SEQ ID NO: 36) |
| VhN95F | 5' GCC AAA GCT GAT CCT GGG 3' (SEQ ID NO: 37) |
| VhN95R | 5' AGG ATC AGC TTT GGC ACA 3' (SEQ ID NO: 38) |
| VhF100KF | 5' ACA GGC GCT GCT TAC TGG GGC 3' (SEQ ID NO: 39) |
| VhF100KR | 5' GTA AGC AGC GCC TGT CCC AGG 3' (SEQ ID NO: 40) |
| VhY102F | 5' GGC TTT GCT GCC TGG GGC CAA GGG 3' (SEQ ID NO: 41) |
| VhY102R | 5' GCC CCA GGC AGC AAA GCC TGT CCC 3' (SEQ ID NO: 42) |
| VhW103F | 5' TTT GCT TAC GCG GGC CAA GGG 3' (SEQ ID NO: 43) |
| VhW103R | 5' TTG GCC CGC GTA AGC AAA GCC 3' (SEQ ID NO: 44) |
| VlY32F | 5' TAC AGT GCT TTA GCA TGG 3' (SEQ ID NO: 45) |
| VlY32R | 5' TGC TAA AGC ACT GTA AAT ATT CTC 3' (SEQ ID NO: 46) |
| VlW35F | 5' TTA GCA GCG TAT CAG CAG 3' (SEQ ID NO: 47) |
| VlW35R | 5' CTG ATA CGC TGC TAA ATA AC 3' (SEQ ID NO: 48) |
| VlY36F | 5' GCA TGG GCT CAG CAG AAA CAG 3' (SEQ ID NO: 49) |
| VlY36R | 5' CTG CTG AGC CCA TGC TAA ATA AC 3' (SEQ ID NO: 50) |
| VlT53F | 5' GCA AAA GCC TTA GCA GAA 3' (SEQ ID NO: 51) |

TABLE I-continued

Primers used for the mutant
Fab 13B8.2 constructions

| NAME | SEQUENCE |
|---|---|
| V1T53R | 5' TGC TAA GGC TTT TGC ATC ATG GAC 3' (SEQ ID NO: 52) |
| V1C88F | 5' TAT TAC GCT CAA CAT CAT TAT GG 3' (SEQ ID NO: 53) |
| V1C88R | 5' ATG TTG AGC CTA ATA AGT CCC 3' (SEQ ID NO: 54) |
| V1H91F | 5' CAA CAT GCT TAT GGT AAT CC 3' (SEQ ID NO: 55) |
| V1H91R | 5' ACC ATA AGC ATG TTG ACA G 3' (SEQ ID NO: 56) |
| V1Y92F | 5' CAT CAT GCT GGT AAT CCT CCG 3' (SEQ ID NO: 57) |
| V1Y92R | 5' ATT ACC AGC ATG ATG TTG ACA G 3' (SEQ ID NO: 58) |

Production of the Recombinant Fab Fragments, Purification and Characterization

Each recombinant Fab of the 13B8.2 antibody was purified on protein G from 400 ml of supernatant of Sf9 *Spodoptera frugiperda* (ATCC CRL 1711) cells infected with recombinant baculovirus as described in [Bès, 2001a].

The purified Fab fragments were quantified by ELISA using a sheep antiserum directed against the human Fdγ$_1$ fragment (THE BINDING SITE™, Birmingham, UK) as capture reagent and an antibody directed against the human kappa chains conjugated with peroxidase (SIGMA™, St Louis, Mo.) as detection reagent. Samples of the antibodies were then tested by electrophoretic and Western blot analysis.

Studies of the Binding of CD4 by the Wild and Mutant Fab Fragments of the 13B8.2 Antibody An ELISA method was implemented for the initial screening of the Fab fragments of the 13B8.2 antibody for their capacity to bind with soluble CD4.

A 1:500 dilution of the CD4 fraction expressed by the baculovirus in 0.1 M carbonate/bicarbonate buffer, pH 9.6, was incubated overnight at 4° C. on 96-well enzymatic immunoanalysis plates (NUNC™, Paisley, UK). Four washings with the phosphate saline buffer (PBS) 160 mM pH 7.2, containing 0.1% Tween 20 (PBD-T), were performed before and after the saturation of the microplates, with powdered skim milk at a concentration of 1% in the PBS-T for one hour at 37° C.

The 100%1 of the dilutions in series two by two of a solution of antibodies at 2.5 µg/ml was added to each well.

After having been incubated for 2 hours and washed in PBS-T, the bound antibodies were detected by addition of 100 µl of 1:1000 solution of conjugated human anti-kappa-peroxidase (Sigma) followed by the addition of the substrate of the peroxidase. The absorbance was measured at 490 nm ($A_{490}$).

The kinetic parameters of the binding of CD4 to the paratope of the Fab fragments of the 13B8.2 antibody were determined by analysis of the surface plasmon resonance by means of a BIACORE™ analyzer (BIACORE AB™, Uppsala, Sweden).

The CD4 expressed in the baculovirus was immobilized in a covalent manner on a biosensor and the recombinant Fabs in HBS buffer (100 mM Hepes, pH 7.6, 150 mM NaCl) were injected at various concentrations between 5 and 20 µg/ml.

The kinetic parameters were calculated using the BIAEVALUATION™, 3.2 evaluation program and the global method according to [Karlsson, 1994].

The binding of the wild or mutant Fabs to the membranous CD4 was evaluated by flow cytometry.

T AN2.01/CD4 ($1 \cdot 10^6$) cells were incubated with PBS containing 0.2% BSA(PBS-BSA) or with PBS-BSA supplemented with each of the recombinant Fabs or with the irrelevant anti-digoxin Fab IC10 expressed in the baculovirus/insect cell systems (1 µg/ml).

Similar experiments were performed with T AN2.01 cells (a negative T Cd4 cell line). After three washings with PBS-BSA, the bound antibodies were revealed by incubation with 50 µl of a 1:1000 solution of an antibody directed against the human kappa light chain conjugated with fluorescein (SIGMA™) over one hour at 4° C. After three subsequent washings with PBS-BSA, the intensity of the fluorescence was measured in an EPICS cytofluorimeter (BECKMAN-COULTER™, Fullerton, Calif.).

Test of Secretion of 112 After Presentation of the Antigen

As described [Bès, 2001a, 2001b], cells presenting EBV-Lu antigen pulsed with the stimulator peptide pep24 ($10^5$ cells/well) were co-cultured with responder T cells pdb 10F ($2 \times 10^4$ cells/well). The wild or mutant Fabs of the 13B8.2 antibody (20 µg/ml) were added to the cells and the presentation of antigen was performed during 24 hours at 37° C. Then 100 µl of supernatant was recovered and tested for the secretion of 112 using a commercial ELISA kit (PHARMINGEN™, San Diego, Calif.).

Test of Activity of the HIV-1 Promoter

HeLa P4 indicator cells ($8 \cdot 10^4$ cells/ml) were cultured in the medium supplemented or not supplemented with the infectious HIV-1$_{Lai}$ virus in the presence (20 µg/ml) or absence of the Fabs for three days, recovered and lysed. The β-galactosidase activity was determined as previously described by measuring the absorbance at 410 nm [Monnet, 1999].

Molecular Modeling of the Variable Regions of the 13B8.2 antibody

A three-dimensional model of the variable regions of the heavy and light chains of the 13B8.2 antibody was obtained using the AbM program (Oxford Molecular, ACCELRYS™, UK) [Rees, 1992] on a O2 R5000 SILICON GRAPHICS™ work station.

The loops L2, L3, H1 and H2-CDR were constructed according to a class 1 canonical frame and a class 2 canonical frame for the loop L1 as defined by the AbM software program.

The loop H3 was constructed using a combined database/CONGEN search. CONGEN is a conformational search program implemented in AbM combined with a search of a database of 3D structures.

The hydrogenes were added to the model using the SYBYL™ software program (TRIPOS™, Inc.) and the model was minimized during 100 iterations with the TRIPOS™ force field and the conjugated gradient method for eliminating all of the small serum conflicts. The surface areas accessible to the solvents of the amino acids of the 13B8.2 antibody were calculated in the 3D model by the SALVOL software program implemented in SYBYL™.

Measurement of the Viral Reverse-Transcriptase Activity

This method, used in the framework of the study of the antiviral properties of the recombinant chimeric Fab fragment of the 13B8.2 antibody, enables measurement of a kinetic of viral proliferation by quantitative determination of the viral reverse-transcriptase activity in the culture supernatant of cells infected by HIV.

The first step consisted of infecting $5 \cdot 10^5$ CEM cells per sample to be tested. This involved, after washing the cells in PBS, incubating them for 30 minutes at 4° C. in the presence of 100TCID$_{50}$ of HIV-1$_{Lai}$ virus (100 µl of virus for $5 \cdot 10^5$ cells). Four steps of washing in RPMI culture medium were then implemented to remove the excess virus. The cells were spread on p24 plates, then cultured for 3 days at 37° C. under 5% $CO_2$ in the presence of the samples to be tested under a final volume of 1 ml. Apart from the samples that were potentially inhibitors of viral proliferation, we also tested the reverse-transcriptase activity in the absence of inhibitor, in the absence of virus and in the presence of known inhibitors such as AZT so as to have multiple internal controls.

The second step consisted of the extraction of the viral reverse-transcriptase. This step could be repeated every 3 days over a period of 15 to 20 days. In order to accomplish this, the culture plate was centrifuged for 3 minutes at 4° C. at 1500 rpm so as to recover the supernatant. The infected cells were returned to culture after readjustment of their concentration to $5 \cdot 10^5$ cells/ml in the presence of the samples to be tested. The culture supernatant was centrifuged for 5 minutes at 4° C. at 95,000 rpm. The deposit obtained, containing the viral particles produced by the infected cells, was incubated for 15 minutes at 4° C. in the presence of 15 µl of lysis buffer (see preparation of the buffers). At this level the lysates of viral particles can be stored at −80° C. for subsequent use.

The third step consisted of quantitative determination of the reverse-transcriptase activity. The lysate was brought into the presence of 40 µl of reaction medium (see preparation of the buffers) and incubated for 1 hours at 37° C. The reaction medium contained an RNA matrix (RNApolyA), a primer (oligodT) and a mixture of four nucleotides including deoxythymidine labeled with $^3$H. This step thus made it possible to monitor the incorporation of $^3$H-dTTP in the retrotranscript by the reverse transcriptase present in the lysate of viral particles. In fact, after stopping the reaction by addition of 1 ml of PPNa 0.1 M in TCA 5% (sodium pyrophosphate in trichloroacetic acid), the retrotranscript DNA was precipitated in the presence of 200 µl of a solution of salmon sperm DNA (500 mg/ml) and 4 ml of 20% TCA for 15 minutes at 4° C. This solution was filtered on a 0.45µ Millipore filter. The filters on which DNA was recovered were washed twice with 5% TCA then dried first with 70% ethanol then in the oven for 10 minutes at 37° C. The radioactivity present on the filters was then measured after incorporation of the filters in 5 ml of scintillating liquid.

Measurement of the reverse-transcriptase activity expressed in cpm/ml enables monitoring of the viral proliferation as a function of time in the presence of the potentially inhibitory samples.

Mixed Lymphocyte Reactions

By this approach, the applicant evaluated the capacity of the recombinant chimeric Fab fragment of the 13B8.2 antibody to inhibit cellular proliferation upon the bringing into contact of two lymphocyte populations originating from the peripheral blood of different donors.

The first step consisted of performing the mixed lymphocyte reaction. To achieve this, buffy coats (lymphocyte preparations of peripheral blood) originating from two different donors A and B were washed in RPMI culture medium (supplemented with 10% of human serum AB, the antibiotics penicillin and streptomycin and L-glutamine). The cells were then diluted in culture medium at the level of $1 \cdot 10^6$ cells/ml. The mixed lymphocyte reaction was performed in p96 culture plates according to two schemas. The first, one-way schema consisted of mixing 50 µl of cell suspension of donor A with 50 µl of a cell suspension of the same concentration and the same donor previously treated for 30 minutes at 37° C., 5% $CO_2$, with mitomycin C (final concentration of 25 µg/ml). This schema makes it possible to evaluate the cellular proliferation in response to abnormal cells. The second two-way schema consists of mixing 100 µl of cell suspensions originating from donors A and B not treated with mitomycin C. This schema makes it possible to evaluate the cellular proliferation in response to foreign cells. As a general rule, this second schema can improve the sensitivity of the result. In both cases, the cells were incubated for 5 to 7 days in the presence of 50 µl of the sample solution to be tested.

The second step consists of the quantitative determination of the cellular proliferation. In order to achieve this, the cells were incubated for 18 hours at 37!C, 5% $CO_2$, in the presence of 20 µM of BrdU. This molecule was incorporated in the DNA of the cells in division. The culture plate was then centrifuged so as to eliminate the supernatant, then dried for 1 hour at 37° C. The cells were then fixed for 30 minutes at 25° C. by addition of 200 µl of FixDenat solution. After washing the excess of fixation solution, the incorporation of BrdU was revealed according to the ELISA principle after incubation for 3 hours at 37° C. in the presence of an anti-BrdU antibody labeled with peroxidase and addition of a colorant substrate. Measurement of the absorbance was performed at 450 nm.

The cellular proliferation was then expressed in absorbance units as a function of the nature and concentration of the tested sample.

Results

Identification of the Contributor Residues of the Paratope of the Antibody to CD4 Binding Seventeen hexapeptides of the previously identified sequences of the variable regions of the 13B8.2 antibody [Bès, 2001b] and series of alanine analogues were synthesized on cellulose membrane by the Spot method in order to more precisely identify the critical residues of the antibodies implicated in the binding to CD4.

Figure 1:
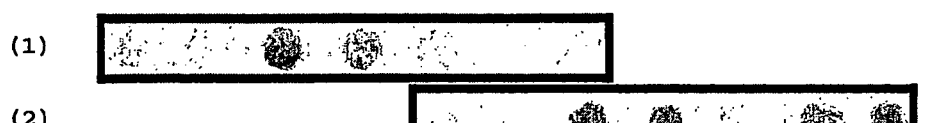
FIG. 1 shows the determination of the residues contributing to the binding to CD4 of the paratope of the 13B8.2 antibody by alanine Spot scanning.
Figure 1:
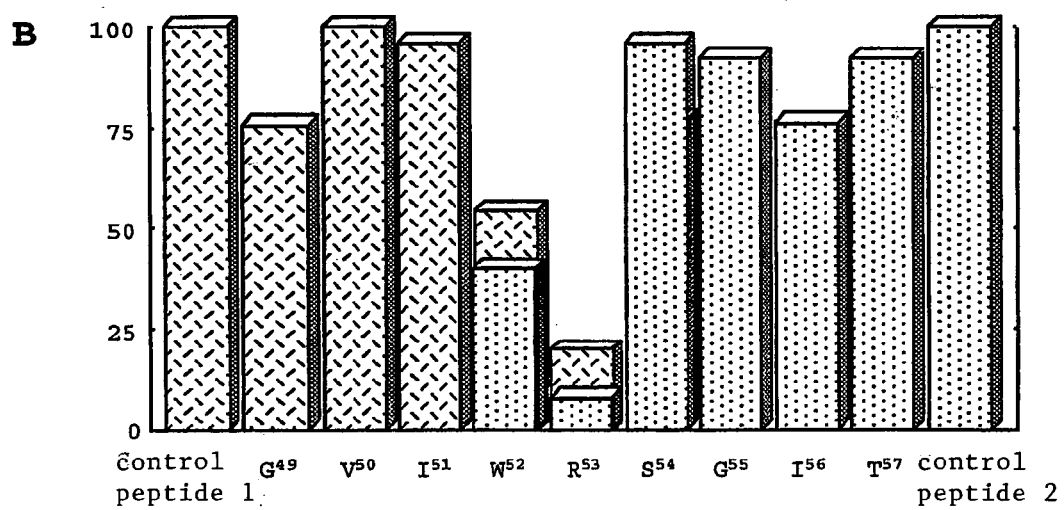
Figure 1:
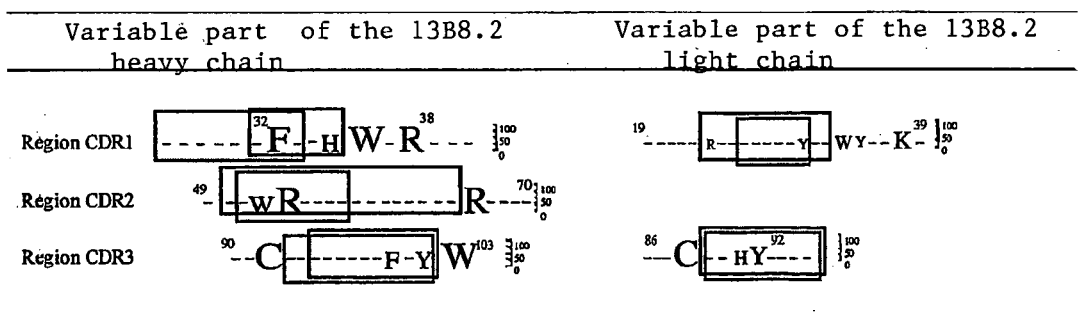

A detailed study of the sequence 49-57 of the CDR-H2 region of the 13B8.2 antibody is shown in attached FIGS. 1A and 1B.

The substitution of Trp$^{52}$ of the peptide $^{49}$GVIWRS$^{54}$ (SEQ ID NO: 62) (defined as control peptide 1) by an alanine residue led to a diminishment by 50% in the capacity of binding to CD4, whereas the change of Arg$^{53}$ led to a total loss of reactivity for the antigen.

The four other replacements of the $^{49}$GVIWRS$^{54}$ (SEQ ID NO: 62) peptide residues by an alanine did not modify their capacity to bind to the antigen.

The contribution of Trp$^{52}$ and Arg$^{53}$ to binding with the CD4 molecule was confirmed by the method of alanine scanning of the $^{52}$WRSGIT$^{57}$ (SEQ ID NO: 63) peptide (FIGS. 1A and 1B).

Similar experiments using the hexapeptides $^{61}$VPFMSR$^{66}$ (SEQ ID NO: 64), $^{65}$SRLSIT$^{70}$ (SEQ ID NO: 65) of the CDR-H2 region and its six alanine analogues enabled identification of the Arg$^{66}$ residue as binding residue of the CD4 molecule (data not presented).

Taken together, it was determined that the contributor motif for the H2 region is $^{52}$WR----------R$^{66}$ (SEQ ID NO: 66) (FIG. 1C) with two residues Trp$^{52}$ and Arg$^{53}$ belonging to the CDR.

In the same manner, the contributor motif $^{32}$F--HW-R$^{38}$ (SEQ ID NO: 67) was determined by Alascan Spot analysis of three hexapeptides $^{31}$TFGVHW$^{36}$ (SEQ ID NO: 68), $^{34}$VHWVRQ$^{39}$ (SEQ ID NO: 69) and $^{36}$WVRQSP$^{41}$ (SEQ ID NO: 70) of the H1 region of the paratope of the 13B8.2 antibody. One of the two residues (Phe$^{32}$, His$^{35}$) according to Kabat's nomenclature of the IGMT (FIG. 1C) is implicated in the CDR.

For the H3 regions, the motif binding to the CD4 molecule $^{95}$C--------F-YW$^{107}$ (SEQ ID NO: 71) comprising the residues Phe$^{104}$ and Tyr$^{106}$ of the CDR and two other framework residues were determined of the three hexapeptides $^{93}$YYCAKN$^{98}$ (SEQ ID NO: 72), $^{95}$CAKNDP$^{100}$ (SEQ ID NO: 73) and $^{102}$TGFAYW$^{107}$ (SEQ ID NO: 74).

The study of the four hexapeptides $^{19}$VTFTCR$^{24}$ (SEQ ID NO: 75), $^{21}$FTCRAS$^{26}$ (SEQ ID NO: 76), $^{32}$YLAWYQ$^{37}$ (SEQ ID NO: 76) and $^{35}$WYQQKQ$^{40}$ (SEQ ID NO: 78) of the L1 region identified the residues Arg$^{24}$, Tyr$^{32}$, Trp$^{35}$, Tyr$^{36}$ and Lys$^{39}$ as contributing to the binding of the CD4 molecule.

Given that there was no reactivity seen in the L2 region [Bès, 2001b], no binding motif was identified.

The motif $^{88}$C--HY$^{92}$ (SEQ ID NO: 79) contributes to the binding by the CD4 molecule according to the results of the SPOT Alascan analysis of the three hexapeptides $^{85}$TYYCQH$^{90}$ (SEQ ID NO: 80), $^{88}$CQHHYG$^{93}$ (SEQ ID NO: 81) and $^{91}$HYGNPP$^{96}$ (SEQ ID NO: 82) of the L3 region with the residues His$^{91}$ and Tyr$^{92}$ belonging to the CDR (FIG. 1C).

Taken in its entirety, 19 residues of the paratope of the 13B8.2 antibody were initially identified as SCR residues binding to the CD4 molecule by SPOT Alascan analysis.

However, among these residues, the residue. Arg$^{66}$ of the heavy chain and the residues Arg$^{24}$ and Lys$^{39}$ of the light chain were found systematically to be weakly accessible to the solvent in the three-dimensional structure of the antibodies and had never previously been identified as being critical residues in the binding of the antigen [McCallun, 1996; Honneger, 2001].

Consequently, only 16 SCRs of the paratope of the 13B8.2 antibody were selected for the subsequently performed directed mutagenesis.

Characterization of the Mutant Fabs, of a Single Alanine, of the 13B8.2 Antibody The genes of the variable regions of the heavy and light chains of the 13B8.2 antibody were used as matrices for a directed mutagenesis by overlapping PCR in order to replace each of the SCRs selected by an alanine residue in the global context of the Fab of the 13B8.2 antibody.

After cloning in the suitable vectors pBHuFd$_{-1}$ or pBHuC_, expression in a baculovirus/insect cell system, purification by means of protein G, each of the mutant Fabs, designated below as F32-H (SEQ ID NO: 3), H35-H (SEQ ID NO: 4), W36-H (SEQ ID NO: 5), R38—H (SEQ ID NO: 6), W52-H (SEQ ID NO: 7), R53—H (SEQ ID NO: 8), C92-H (SEQ ID NO: 9), F 100K-H (SEQ ID NO: 10), Y102-H (SEQ ID NO: 11) and W103-H (SEQ ID NO: 12) for those presenting mutations on the variable domain of the heavy chain and Y32-L (SEQ ID NO: 13), W35-L (SEQ ID NO: 14), Y36-L (SEQ ID NO: 15), C88-L (SEQ ID NO: 16), H91-L (SEQ ID NO: 17) and Y92-L (SEQ ID NO: 18) for those presenting mutations on the variable domain of the light chain were furthermore detected and quantified by ELISA and Western blot for the production of immunoglobulins (FIGS. 2A and 2B).

The sequences of the regions of the VH and VL domains of each of the mutant Fabs in relation to the corresponding sequences of the VH (SEQ ID NO: 1) and VL (SEQ ID NO: 2) domains of the wild Fab of the 13B8.2 antibody are presented in Table II (domain VH) and Table III (domain VL) below.

TABLE II

VH domain 13B8.2

| | | | | | | | | | | | | | | | | | | | | |
|---|---|---|---|---|---|---|---|---|---|---|---|---|---|---|---|---|---|---|---|---|
| | | | | | | | | | | | | | | | | | CDR1 VH | | | |
| | 1 | | | | | 11 | | | 21 | | | | | | | 30 | | | 40 | |
| VH wild | QV | Q | L | K | QSGPG | L | VQPSQ | S | LSI | T | C | T | V | S | GFSL | T | TF | G | VHWVRQ | S |
| P32-H | -- | - | - | - | ----- | - | ----- | - | --- | - | - | - | - | - | ---- | - | -A | - | ------ | - |
| H35-H | -- | - | - | - | ----- | - | ----- | - | --- | - | - | - | - | - | ---- | - | -- | - | -A---- | - |
| W36-H | -- | - | - | - | ----- | - | ----- | - | --- | - | - | - | - | - | ---- | - | -- | - | --A--- | - |
| R38-H | -- | - | - | - | ----- | - | ----- | - | --- | - | - | - | - | - | ---- | - | -- | - | ----A- | - |
| W52-H | -- | - | - | - | ----- | - | ----- | - | --- | - | - | - | - | - | ---- | - | -- | - | ------ | - |
| R53-H | -- | - | - | - | ----- | - | ----- | - | --- | - | - | - | - | - | ---- | - | -- | - | ------ | - |
| C92-H | -- | - | - | - | ----- | - | ----- | - | --- | - | - | - | - | - | ---- | - | -- | - | ------ | - |
| F100K-H | -- | - | - | - | ----- | - | ----- | - | --- | - | - | - | - | - | ---- | - | -- | - | ------ | - |
| Y102-H | -- | - | - | - | ----- | - | ----- | - | --- | - | - | - | - | - | ---- | - | -- | - | ------ | - |
| W103-H | -- | - | - | - | ----- | - | ----- | - | --- | - | - | - | - | - | ---- | - | -- | - | ------ | - |
| Y32-L | -- | - | - | - | ----- | - | ----- | - | --- | - | - | - | - | - | ---- | - | -- | - | ------ | - |
| W35-L | -- | - | - | - | ----- | - | ----- | - | --- | - | - | - | - | - | ---- | - | -- | - | ------ | - |
| Y36-L | -- | - | - | - | ----- | - | ----- | - | --- | - | - | - | - | - | ---- | - | -- | - | ------ | - |
| C88-L | -- | - | - | - | ----- | - | ----- | - | --- | - | - | - | - | - | ---- | - | -- | - | ------ | - |
| H91-L | -- | - | - | - | ----- | - | ----- | - | --- | - | - | - | - | - | ---- | - | -- | - | ------ | - |
| Y92-L | -- | - | - | - | ----- | - | ----- | - | --- | - | - | - | - | - | ---- | - | -- | - | ------ | - |

| | | | | | | | | | | | | | | | | | | | | | | |
|---|---|---|---|---|---|---|---|---|---|---|---|---|---|---|---|---|---|---|---|---|---|---|
| | | | | | | | | CDR2 VH | | | | | | | | | | | | | | |
| | 41 | | | | | 51 | | | | | 61 | | | | | | 70 | | | | 80 | |
| VH wild | P | G | K | G | L | EWLGV | I | WRSGI | T | DYN | V | P | F | M | S | RLSI | T | KD | N | SKS | Q | VF | F |
| P32-H | - | - | - | - | - | ----- | - | ----- | - | --- | - | - | - | - | - | ---- | - | -- | - | --- | - | -- | - |
| H35-H | - | - | - | - | - | ----- | - | ----- | - | --- | - | - | - | - | - | ---- | - | -- | - | --- | - | -- | - |
| W36-H | - | - | - | - | - | ----- | - | ----- | - | --- | - | - | - | - | - | ---- | - | -- | - | --- | - | -- | - |

TABLE II-continued

VH domain 13B8.2

```
R38-H     - - -  -  - -----  -  - ---  -  - ----  -  - ---  -- -
W52-H     - - -  -  - -----  A----  -  - ----  -  - ---  -- -
R53-H     - - -  -  - -----  -A---  -  - ----  -  - ---  -- -
C92-H     - - -  -  - -----  -----  -  - ----  -  - ---  -- -
F100K-H   - - -  -  - -----  -----  -  - ----  -  - ---  -- -
Y102-H    - - -  -  - -----  -----  -  - ----  -  - ---  -- -
W103-H    - - -  -  - -----  -----  -  - ----  -  - ---  -- -
Y32-L     - - -  -  - -----  -----  -  - ----  -  - ---  -- -
W35-L     - - -  -  - -----  -----  -  - ----  -  - ---  -- -
Y36-L     - - -  -  - -----  -----  -  - ----  -  - ---  -- -
C88-L     - - -  -  - -----  -----  -  - ----  -  - ---  -- -
H91-L     - - -  -  - -----  -----  -  - ---   -  - ----  -- -
Y92-L     - - -  -  - -----  -----  -  - ----  -  - ---  -- -
```

```
                                                    VH
        81 82 82A 82B 82C 83    88       94|   99  100J100K101|   106       113
VH      K  L  N   S   L   Q  PDDT A IYYCA K NDPG  T    G    F    A YWGQ G TLVTVS A
wild
P32-H   -  -  -   -   -   -  ----  - -----  - ----  -    -    -    - ----  - ------ -  ---
H35-H   -  -  -   -   -   -  ----  - -----  - ----  -    -    -    - ----  - ------ -  ---
W36-H   -  -  -   -   -   -  ----  - -----  - ----  -    -    -    - ----  - ------ -  ---
R38-H   -  -  -   -   -   -  ----  - -----  - ----  -    -    -    - ----  - ------ -  ---
W52-H   -  -  -   -   -   -  ----  - -----  - ----  -    -    -    - ----  - ------ -  ---
R53-H   -  -  -   -   -   -  ----  - -----  - ----  -    -    -    - ----  - ------ -  ---
C92-H   -  -  -   -   -   -  ----  - ---A-  - ----  -    -    -    - ----  - ------ -  ---
F100K-H -  -  -   -   -   -  ----  - -----  - ----  -    -    A    - ----  - ------ -  ---
Y102-H  -  -  -   -   -   -  ----  - -----  - ----  -    -    -    - A---  - ------ -  ---
W103-H  -  -  -   -   -   -  ----  - -----  - ----  -    -    -    - -A--  - ------ -  ---
Y32-L   -  -  -   -   -   -  ----  - -----  - ----  -    -    -    - ----  - ------ -  ---
W35-L   -  -  -   -   -   -  ----  - -----  - ----  -    -    -    - ----  - ------ -  ---
Y36-L   -  -  -   -   -   -  ----  - -----  - ----  -    -    -    - ----  - ------ -  ---
C88-L   -  -  -   -   -   -  ----  - -----  - ----  -    -    -    - ----  - ------ -  ---
H91-L   -  -  -   -   -   -  ----  - -----  - ----  -    -    -    - ----  - ------ -  ---
Y92-L   -  -  -   -   -   -  ----  - -----  - ----  -    -    -    - ----  - ------ -  ---
```

TABLE III

Domaine VL 3B8.2

```
                                            CDR1
                                          VL kappa
        1           11              21  | 2728     31 |       40
VH      DIQMTQSPAS L S    A     S VGETVT F T CRAS E M IY  S YLAWYQQK Q
wild
P32-H   ---------- - -    -     - ------ - - ----  - -  --  -  ---------- -
H35-H   ---------- - -    -     - ------ - - ----  - -  --  -  ---------- -
W36-H   ---------- - -    -     - ------ - - ----  - -  --  -  ---------- -
R38-H   ---------- - -    -     - ------ - - ----  - -  --  -  ---------- -
W52-H   ---------- - -    -     - ------ - - ----  - -  --  -  ---------- -
R53-H   ---------- - -    -     - ------ - - ----  - -  --  -  ---------- -
C92-H   ---------- - -    -     - ------ - - ----  - -  --  -  ---------- -
F100K-H ---------- - -    -     - ------ - - ----  - -  --  -  ---------- -
Y102-H  ---------- - -    -     - ------ - - ----  - -  --  -  ---------- -
W103-H  ---------- - -    -     - ------ - - ----  - -  --  -  ---------- -
Y32-L   ---------- - -    -     - ------ - - ----  - -  --  -  A------- -
W35-L   ---------- - -    -     - ------ - - ----  - -  --  -  ---A---- -
Y36-L   ---------- - -    -     - ------ - - ----  - -  --  -  ----A--- -
C88-L   ---------- - -    -     - ------ - - ----  - -  --  -  ---------- -
H91-L   ---------- - -    -     - ------ - - ----  - -  --  -  ---------- -
Y92-L   ---------- - -    -     - ------ - - ----  - -  --  -  ---------- -
```

```
                    CDR2
                   VL kappa
        41      | 51             |  61          71        80
VH      G KSPQLLVHD A  K    T    L AEGVPS R FSGGGSGTQ F SLKINTLQ P
wild
P32-H   - --------- -  -    -    - ------  - ---------  - -------- -
H35-H   - --------- -  -    -    - ------  - ---------  - -------- -
W36-H   - --------- -  -    -    - ------  - ---------  - -------- -
R38-H   - --------- -  -    -    - ------  - ---------  - -------- -
W52-H   - --------- -  -    -    - ------  - ---------  - -------- -
R53-H   - --------- -  -    -    - ------  - ---------  - -------- -
C92-H   - --------- -  -    -    - ------  - ---------  - -------- -
F100K-H - --------- -  -    -    - ------  - ---------  - -------- -
```

TABLE III-continued

Domaine VL 3B8.2

```
Y102-H    - ---------- - -    -     -    ------ - ---------  -   -------- -
W103-H    - ---------- - -    -     -    ------ - ---------  -   -------- -
Y32-L     - ---------- - -    -     -    ------ - ---------  -   -------- -
W35-L     - ---------- - -    -     -    ------ - ---------  -   -------- -
Y36-L     - ---------- - -    -     -    ------ - ---------  -   -------- -
C88-L     - ---------- - -    -     -    ------ - ---------  -   -------- -
H91-L     - ---------- - -    -     -    ------ - ---------  -   -------- -
Y92-L     - ---------- - -    -     -    ------ - ---------  -   -------- -
```

```
                              CDR3
                             VL kappa
          81         | 91        |    101        107
VH        E DFGTYYCQH H Y   G    N   PPTFGG   G  TKLEI   K
wild      - ---------- - -  -    -   ------   -  -----   -
P32-H     - ---------- - -  -    -   ------   -  -----   -
H35-H     - ---------- - -  -    -   ------   -  -----   -
W36-H     - ---------- - -  -    -   ------   -  -----   -
R38-H     - ---------- - -  -    -   ------   -  -----   -
W52-H     - ---------- - -  -    -   ------   -  -----   -
R53-H     - ---------- - -  -    -   ------   -  -----   -
C92-H     - ---------- - -  -    -   ------   -  -----   -
F100K-H   - ---------- - -  -    -   ------   -  -----   -
Y102-H    - ---------- - -  -    -   ------   -  -----   -
W103-H    - ---------- - -  -    -   ------   -  -----   -
Y32-L     - ---------- - -  -    -   ------   -  -----   -
W35-L     - ---------- - -  -    -   ------   -  -----   -
Y36-L     - ---------- - -  -    -   ------   -  -----   -
C88-L     - ---------- - -  -    -   ------   -  -----   -
H91-L     - ---------- A -  -    -   ------   -  -----   -
Y92-L     - ---------- - A  -    -   ------   -  -----   -
```

As shown by the examples for the mutants Y36-L, C88-L, F32-H, H35-H, W52-H and R53—H, the production of immunoglobulin was demonstrated for each purified recombinant Fab, as revealed by a capture antibody directed against the heavy chain and revealed by an antibody directed against the kappa chain conjugated to peroxidase.

Figure 2:
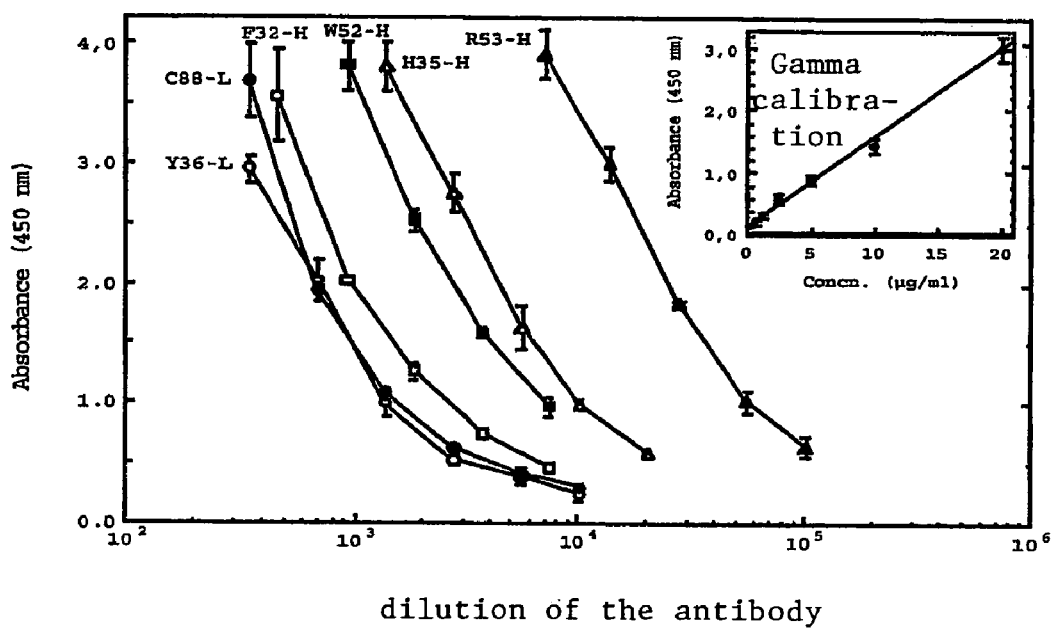
FIG. 2 illustrates the characterization of the recombinant Fab fragments having residues mutated by alanines after immunopurification on protein G from baculovirus supernatants.
Figure 2:
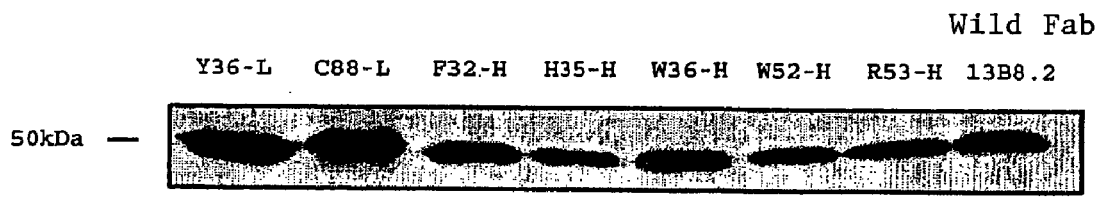

Electrophoretic analyses on acrylamide in the presence of SDS (PAGE-SDS) by coloration with Coomassie blue performed with 1 µg of charged protein for each recombinant Fab revealed a single band at 50 kDa (data not presented) corresponding to the anticipated size of a correctly recombined Fab under non-reducing conditions; the identity of the band at 50 kDa was then confirmed by Western blot using an antibody directed against the human kappa chain (FIG. 2B).

Binding Capacity of the CD4 Molecule by the Mutant Fabs Versus the Wild Fab of the 13B8.2 Antibody The capacity of the mutant Fabs versus the wild Fab for binding the soluble CD4 molecule was first verified by an ELISA method (FIG. 3) and then quantified by BIACORE™ analysis (Table IV below).

TABLE IV

Determination by BIACORE ™ of the kinetics of interaction between CD4 fixed on 13B8.2 antibody(ies)

| Antibody | | $k_a$ $10^4 s^{-1} M^{-1}$ | $K_d$ $10^{-4} s^{-1}$ | $K_D$ nM |
|---|---|---|---|---|
| Fab wild 13B8.2 | Exp. 1 | 0.38 | 1.08 | 28.4 |
| | Exp. 2 | 0.48 | 1.61 | 33.5 |
| | Exp. 3 | 0.25 | 0.64 | 25.6 |
| Fab$_{control}$1C10 | | NM | NM | NM |
| Fab mutants 13B8.2 | | | | |
| Y32-L | | 0.00655 | 5.85 | 8931.2 |
| W35-L | Exp. 1 | 4.94 | 9.23 | 18.7 |
| | Exp. 2 | 6.60 | 8.41 | 17.0 |
| Y36-L | Exp. 1 | 2.56 | 6.51 | 25.4 |
| | Exp. 2 | 0.50 | 5.70 | 11.4 |
| T53-L$_{control}$ | | 2.21 | 3.65 | 16.5 |
| C88-L | | 3.80 | 4.09 | 10.8 |
| H91-L | | 0.0239 | 40.40 | 16903.7 |
| Y92-L | Exp. 1 | 7.47 | 12.70 | 17.0 |
| | Exp. 2 | 7.07 | 8.89 | 12.5 |
| F32-H | Exp. 1 | 1.83 | 2.48 | 13.5 |
| | Exp. 2 | 1.44 | 2.46 | 17.0 |
| | Exp. 3 | 1.48 | 2.50 | 16.9 |
| H35-H | | 0.0301 | 18.90 | 6279.0 |
| W36-H | | 1.76 | 2.71 | 15.4 |
| R38-H | | 0.0163 | 1.40 | 858.8 |
| W52-H | | 0.0237 | 8.59 | 3624.4 |
| R53-H | | 0.0359 | 105.00 | 29247.9 |
| V61-Hcontrol | Exp. 1 | 8.68 | 1.72 | 2.0 |
| | Exp. 2 | 11.20 | 3.24 | 2.9 |
| C92-H | | 9.61 | 3.58 | 3.7 |
| F100<-H | | 0.0562 | 4.75 | 845.1 |
| Y102-H | | nd[b] | nd | nc[c] |
| W103-H | | 0.0278 | 11.2 | 4028.7 |

[a]Not
[b]Not
[c]Not calculated

In ELISA, the binding activity to CD4 of the wild Fab was demonstrated in the range from 19.5 to 1250 ng/ml (FIG. 2) whereas no binding was seen with the IC10 anti-digoxin recombinant Fab.

Dose-dependent reactivities for CD4 similar to those seen for the wild Fab were demonstrated for the T53-L and V61-H control mutant Fabs as well as for the mutant Fabs on the positions characterized in Spot, C88-L, F32-H, W36-H, C92-H and Y102-H.

Figure 3:
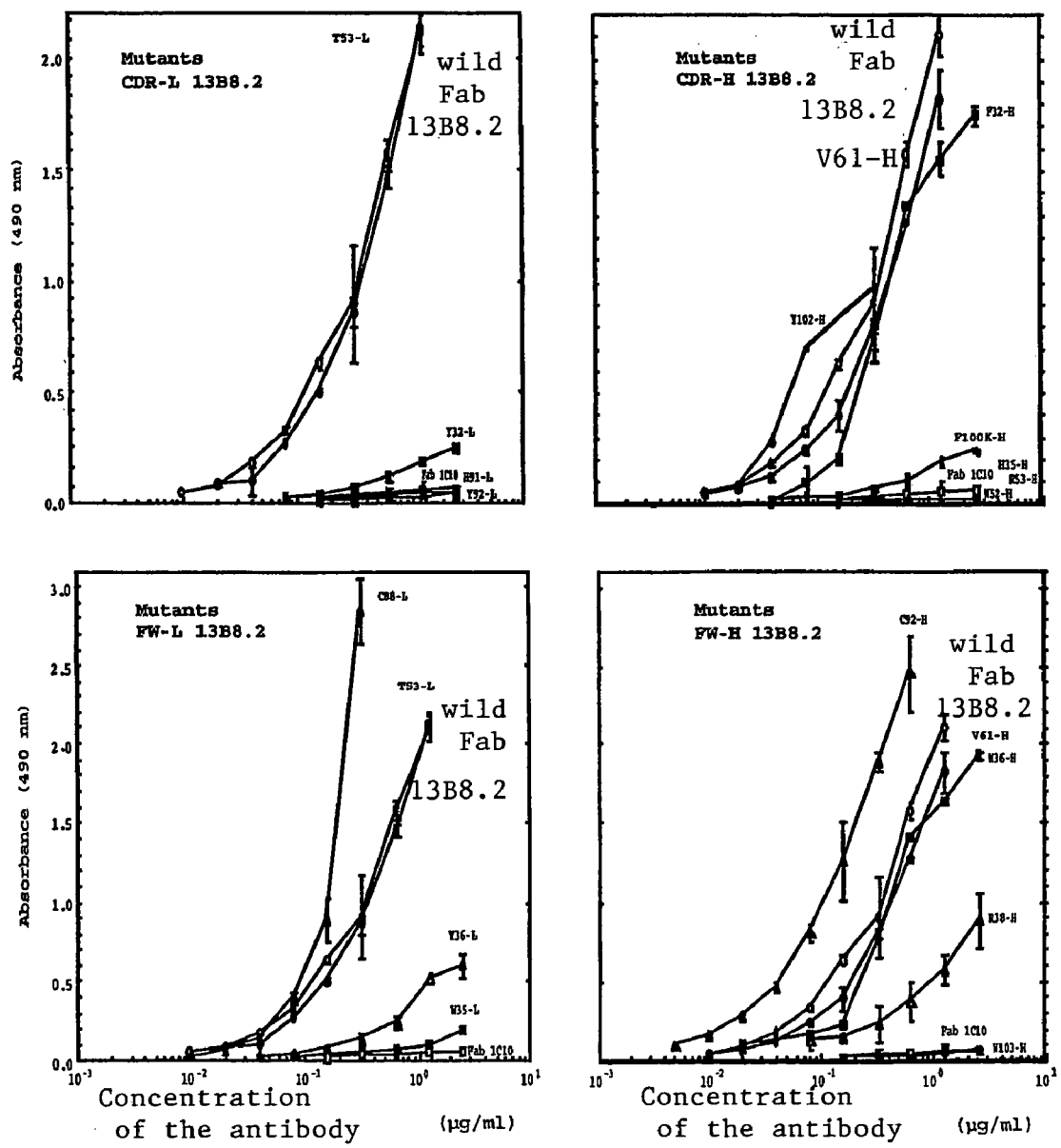
FIG. 3 shows the binding curves obtained by an ELISA method for the mutant Fab fragments of the 13B8.2 antibody on the CD4 molecule absorbed in relation to those obtained with the wild Fab and a Fab1C10 control, each value representing the mean±S.D. of the determinations by triplicate and are representative of three different experiments.
Figure 4:
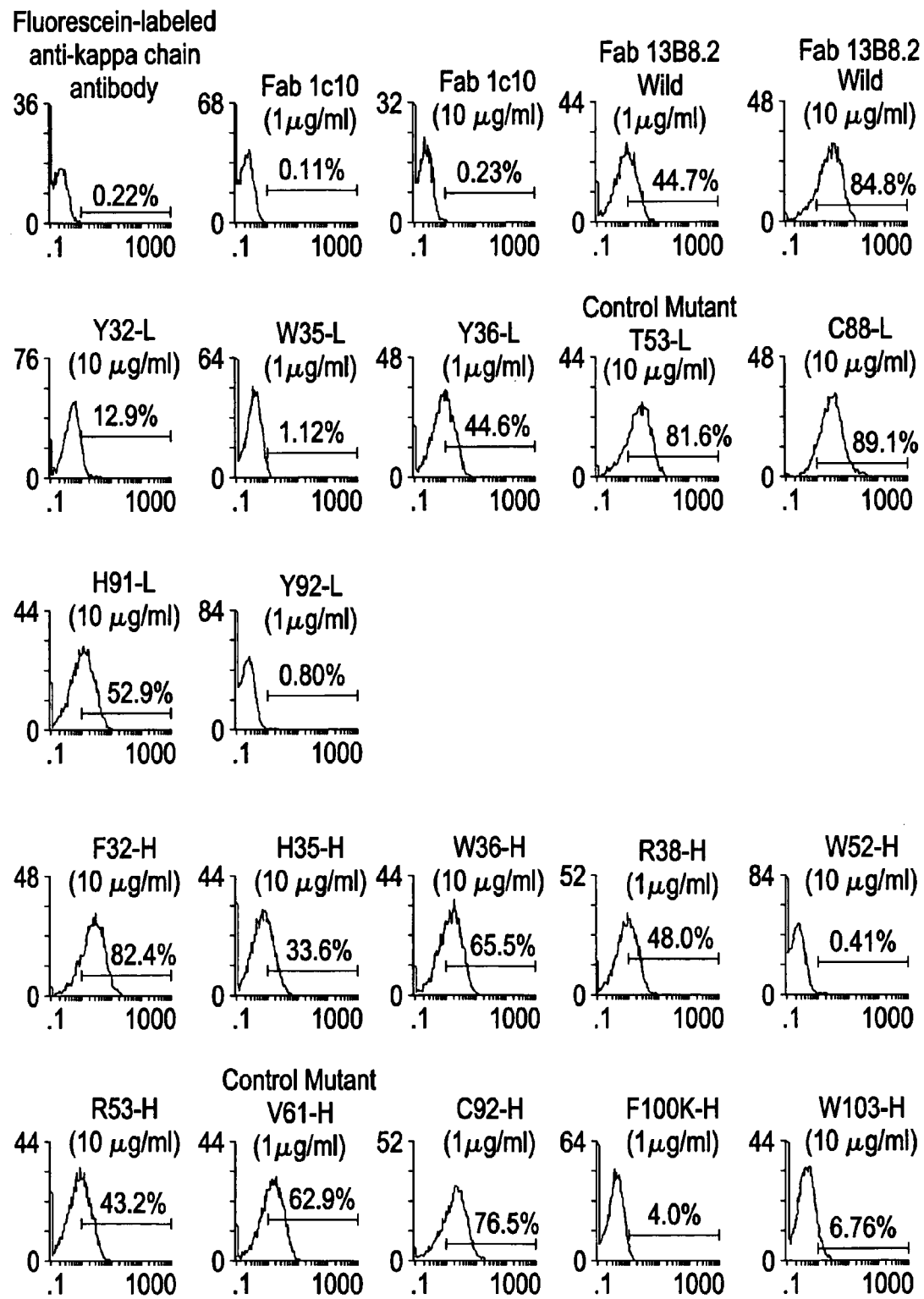
FIG. 4 shows the analysis by flow cytometry of the binding of the T A2.01/CD4 cells of each of the recombinant Fab fragments of the 13B8.2 antibody versus the wild Fab and a Fab 1C10 control. The results are representative of two different experiments. The concentration of antibodies is indicated.
Figure 5:
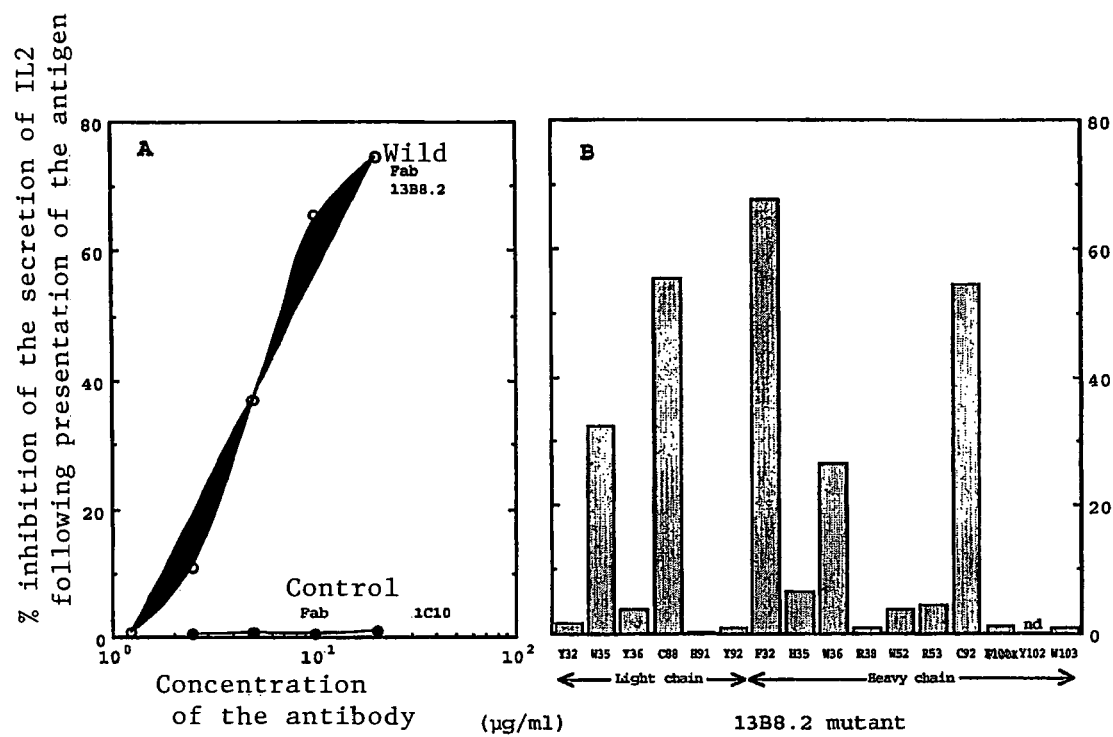
FIG. 5 shows the inhibition of the secretion of 112 by T pdb 10f cells sensitized with cells presenting EBV-Lu antigen stimulated with the peptide pep24 and co-cultured with the recombinant Fab fragments of the 13B8.2 antibody.
Figure 6:
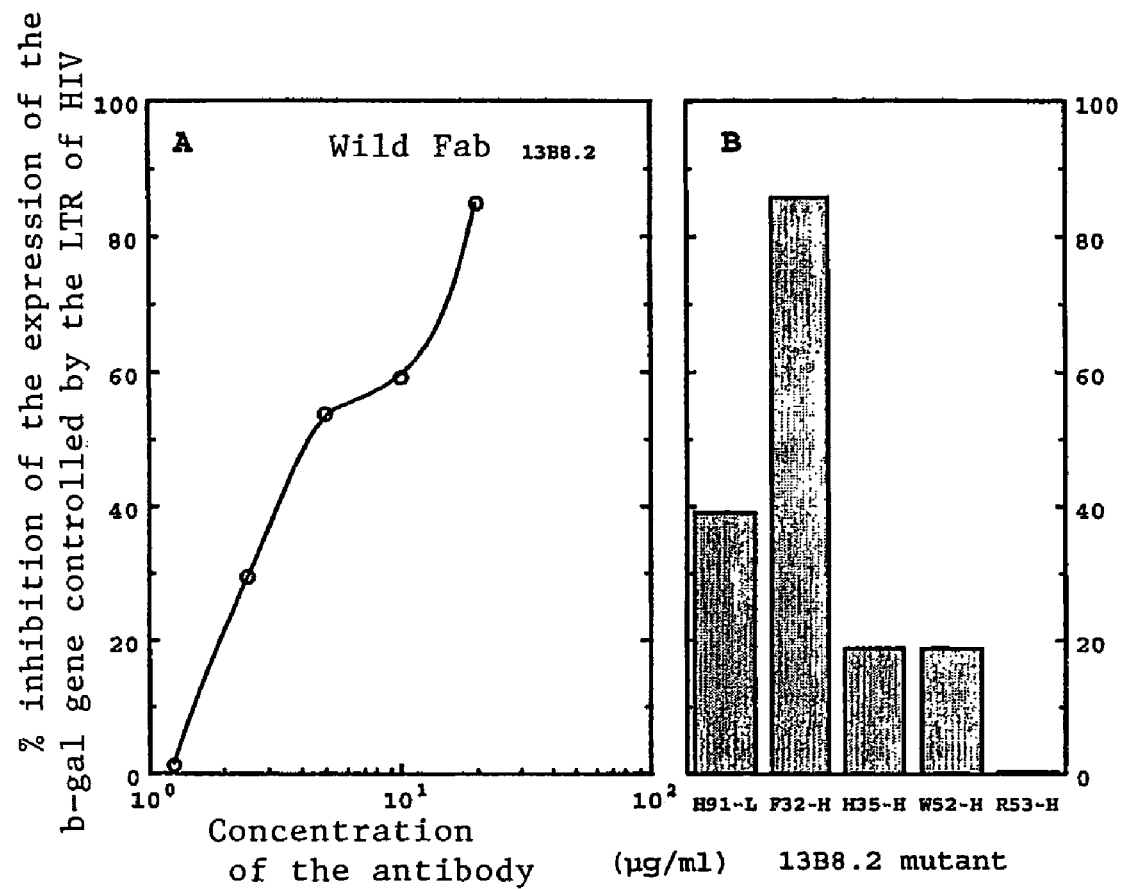
FIG. 6 shows the inhibition of the expression of the gene of galactosidase controlled by the LTR of the HIV-1$_{Lai}$ after incubation with the mutant recombinant Fab fragments of the 13B8.2 antibody.
Figure 7:
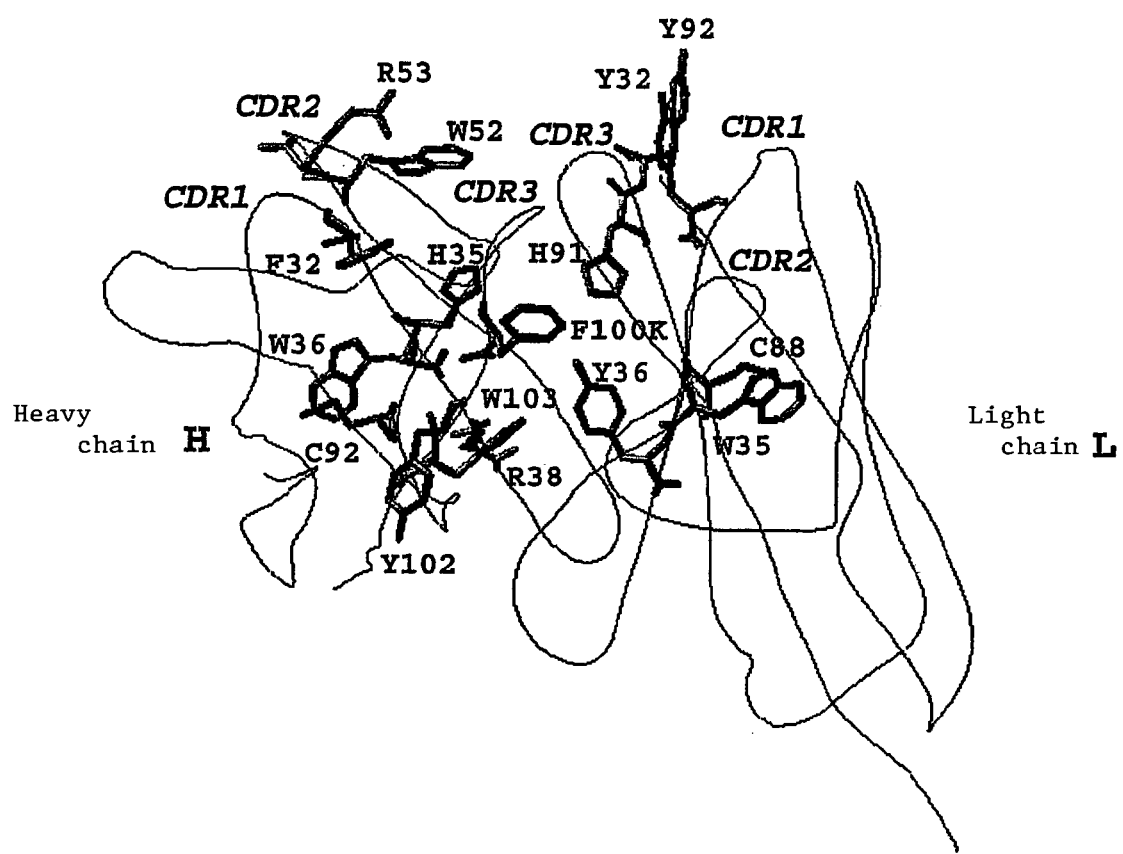
FIG. 7 shows a three-dimensional model of the variable regions of the heavy and light chains of the 13B8.2 antibody generated by the AbM software program based on a homology modeling (frontal view). The computer-based model is shown as a Cα tracing with the lateral chains for each contributing residue selected by Spot for the paratope of the 13B8.2 antibody.

Moreover, the mutation of an alanine at the level of the residues characterized in Spot Tyr$^{32}$, His$^{91}$ and Tyr$^{92}$ of the CDR-L regions, His$^{35}$, Trp$^{52}$, Arg$^{53}$ and Phe$^{100K}$ of the CDR-H regions, Trp$^{35}$ and Tyr$^{36}$ of the FWs regions of the light chain and Arg$^{38}$ and Trp$^{103}$ of the FWs regions of the heavy chain affected the binding to the CD4 molecule in a dose-dependent manner (FIG. 3).

These results were confirmed by means of the BIO-CORE™ technology given that most of the mutant Fabs presenting a loss of their capacity for binding the CD4 molecule by ELISA, such as the Fabs Y32-L, H91-L, H35-H, R38—H, W52-H, R53—H, F100K-H and W103-H exhibited a diminishment of $K_D$ on the order of 100 to 1000 times, whereas those that demonstrated retention of their capacity to bind to the CD4 molecule in ELISA, exhibited $K_D$ values similar to those calculated for the wild Fab of the 13B8.2 antibody (Table IV). Lastly, the mutant Fabs W35-L, Y36-L and Y92-L presenting a diminishment of their capacity to bind to the CD4 molecule in ELISA exhibited $K_D$ values similar to those of the wild Fab of the 13B8.2 antibody but with a higher dissociation rate.

In order to determine the binding of the fragments to the membranous CD4, T AN2.01 CD4+ cells were analyzed by indirect immunofluorescent labeling and flow cytometry (FIG. 4).

A strong coloration of the T cells was obtained with the wild Fab of the 13B8.2 antibody in a dose-dependent manner, whereas the controls with the anti-digoxin IC10 Fab and the anti-kappa chain antibody labeled with fluorescein did not bind to said cells.

Similar experiments using negative T AN2.01 CD4 cells showed that there is no nonspecific binding with the wild Fab nor with the Fabs having their corresponding mutant alanines.

Moreover, a failure in the binding to the CD4 molecule of the cells was seen for the mutants having an alanine replacement on the $Tyr^{332}$, $Trp^{35}$, $His^{91}$ and $Tyr^{92}$ residues of the light chain and the $His^{35}$, $Trp^{52}$ $Arg^{53}$, $Phe^{100K}$ and $Trp^{103}$ residues of the heavy chain.

Biological activities of the Fabs having residues mutated into alanine in relation to the wild Fab of the 13B8.2 antibody in the responses implicating the CD4 molecule.

EBV-Lu antigen presenting cells (APC) stimulated with the peptide Pep24 co-cultured with pdb10F responding T cells led to the lymphocyte secretion of I12 following the presentation of antigen.

As shown in FIG. 5, a dose-dependent inhibition of the secretion of 112 was shown subsequent to the incubation of the wild anti-CD4 Fab of the 13B8.2 antibody in this T cell activation model.

At the same concentrations, the IC10 control Fab did not exhibit any inhibitory activity.

The mutant Fabs exhibiting a capacity to bind to the CD4 molecule similar to that of the wild Fab, such as C88-L, F32-H, W36-H and C92-H, also maintained their inhibitory properties on the presentation of antigen.

In contrast, the other mutations at the level of the SCRs totally or partially abolished the inhibition of the function of presentation of the antigen of the mutant anti-CD4 Fabs (FIG. 5).

These results correlated with the results obtained from the study of the inhibitory properties of the mutant Fabs H91-L, F32-H, H35-H, W52-H and R53—H versus the wild Fab in the promoter activity of HIV-1 (FIG. 6). In this case, the mutant Fabs exhibiting a failure in their capacity to bind the CD4 molecule (H1-L, H35-H, W53-H and R53-H) are not capable of blocking the expression of the reporter gene of β-galactosidase under control of the LTR of HIV-1, whereas the F32 mutant Fab, with a capacity to bind the CD4 molecule preserved like the wild Fab, inhibits the expression of the reporter gene.

Considered all together, the alanine mutations, previously identified in Spot, lead to a failure of the binding to the CD4 molecule correlated with a defect in the biological activities of the mutant Fabs.

Structural analysis of the binding of the mutant Fabs to the CD4 from a computer-based model of the variable regions of the 13B8.2 antibody.

A three-dimensional model of the paratope of the 13B8.2 antibody was obtained by effecting the alignment of the amino acids of the sequence of the 13B8.2 monoclonal antibody with the AbM library sequences according to the definition of frameworks of canonical classes in AbM and a conformational search technique using CONGEN for the CDR H3 (FIG. 7).

The structure of the antibodies Ifd1 and In1d provided the matrix for the FWs regions of the light and heavy chains of the 13B8.2 antibody respectively.

The CDRs, with the exception of CDR-H3, were constructed on the basis of the canonical classes.

Loops known to have the most homologous sequences of the same canonical class were used.

CDR-L1, CDR-L2 and CDR-L3 were constructed using the three-dimensional structure of the 1fd1 antibody and CDR-H1 and CDR-H2 were constructed using the 1n1d structure.

The flexible loop CDR-H3 has not been described as a canonical class and was constructed using a search of the databases combined with a conformational search (CONGEN).

As anticipated, the structure presents two disulfide bridges between the Cys 22 and 92 and the beta sheet of the heavy chain and the Cys23 and 88 residues of the beta sheet of the light chain.

Analysis of the accessibility to the solvent of the amino acids of the 13B8.2 antibody and the orientation of the lateral chains of the critical residues showed that most of the SCRs binding the CD4 molecule confirmed by directed mutagenesis were oriented structurally in the interior of the site of combination with CD4.

Moreover, the mutant Fabs at the level of the $Phe^{32}$, $Trp^{36}$, $Cys^{92}$, $Tyr^{102}$ and $Cys^{88}$ residues, the mutations of which do not alter the binding to CD4 in the context of the entire Fab, show that their lateral chains are not accessible to the solvent ($Cys^{92}$, $Trp^{36}$, $Cys^{88}$) or point in a direction opposite that of the principal orientation of the pocket of CD4 binding, like $Phe^{32}$ and $Tyr^{102}$, thereby confirming structurally that their contribution to the binding to CD4 is improbable.

More specifically, the two cysteines are not accessible to the solvent and are implicated in the disulfide bridges which diminish their probability of interacting with CD4.

Most of the SCR contact residues confirmed by directed mutagenesis are aromatic residues and/or charged residues.

At the entry to a binding site with the antigen corresponding to a surface area of 150 square Å, the residues $Trp^{52}$ and $Arg^{53}$ of the loop CDR-H2 and the residues $Tyr^{32}$ and $Tyr^{92}$ of the loops CDR-L1 and CDR-L3 respectively contribute from each side to the binding with CD4. The residue $Tyr^{30}$ of the loop CDR-L1 is also exposed to the solvent and constitutes a hydrophobic patch with the residues $Tyr^{32}$ and $Tyr^{92}$.

The bottom of the site of binding to CD4, covering a surface area of 75 square A, is constituted by a cluster of aromatic residues, principally charged positively, defined as the residues $His^{35}$, $Phe^{100K}$ of the loops CDR-H1 and the loops CDR-H3 respectively and $His^{91}$ of the region CDR-L3.

Four additional residues ($Arg^{38}$, $Trp^{103}$ of the heavy chain and $Trp^{35}$ and $Tyr^{36}$ of the light chain) with a weak accessibility to the solvent and belonging essentially to the FW, probably stabilize the conformations of the skeleton of the regions implicated in the CD4 binding pocket or shape the H/L interface of the antibody.

The presence of three positively charged residues subjacent to the entry ($Arg^{53}$ of CDR-H2) and the center of the CD4 binding site ($His^{35}$ of CDR-H1 and $His^{91}$ of CDR-L3) suggests that electrostatic interactions could constitute one of the major elements of the binding between the 13B8.2 antibody and its epitope on the homologous region of CDR3 on the CD4 molecule.

Analysis by molecular modeling of the region CDR-L2 showed that the loop L2 is relatively well exposed, explaining the reason for which the activity of nonbinding of CD4 was previously demonstrated by the Spot method [Bès, 2001b].

The definition of critical residue implicated in the binding with the antigen of a paratope of a given antibody is a required condition for guiding the construction of variants with improved activities.

X-ray crystallography sometimes combined with directed mutagenesis and/or molecular modeling is a method of choice for the development of sites of antigen/antibody combination.

Such analyses of the structural paratope (with atomic coordinates) are however limited to certain complexes, dependent on the availability of the antigen and the antibody (noteworthy amounts are often required), the level of post-translational modifications of the antigen and the quality of the crystallogenesis of the complex, these being particularly crucial for the proteins of large size.

In February 2002, the atomic coordinates of the antigen/antibody complexes of approximately only twenty different proteins were described in the Protein Data Bank.

We have now proved that the Spot method in parallel with peptide synthesis constitutes a complementary approach for the fine mapping of the critical residues of the paratope of an antibody implicated in binding with the antigen, free from the previously cited limitations.

This mapping technique has a particular value for proteins that are not available in large quantities. In order to be able to perform such experiments, it is sufficient to have available the amino acid sequences of the variable regions of an antibody, small quantities of antigen and the Spot peptide synthesis technique.

Starting with the 13B8.2 anti-CD4 antibody, approximately 70% of the residues binding to the CD4 molecule, according to analyses performed by the Spot method, were confirmed by directed mutagenesis. These results correlated with the previous indirect arguments indicating that a certain number of residues selected via the somatic mutations of an anti-troponin antibody were contributing residues in the Spot format [Laune, 2002] and that 65% of the SCR residues identified by an anti-lysozyme antibody [Laune, 1998] correlated with the contributing residues previously defined by X-ray crystallography of the lysozyme/HyHel-5 complex [Scheriff, 1987; Cohen, 1996].

Moreover, ten among eleven SCR residues implicated in the binding to the CD4 molecule ($Tyr^{32}$, $Trp^{35}$, $Tyr^{36}$, $His^{91}$ and $Tyr^{92}$ of the light chain of the 13B8.2 antibody; $His^{35}$, $Trp^{52}$, $Arg^{53}$, $Phe^{100K}$ and $Trp^{103}$ of the heavy chain of the 13B8.2 antibody) are localized in positions already identified as being sites of contact with the CD4 molecule [McCallum, 1996; Honneger, 2001], whereas four residues out of five, excluded from the paratope of CD4 by directed mutagenesis do not belong to this "contact" class.

It is interesting that although it is localized in a position already defined as being in contact with the antigen [McCallum, 1996; Honneger, 2001], the last residue $Phe^{32}$ of the heavy chain of the 13B8.2 antibody has not been referenced as a critical amino acid residue in this position [Honneger, 2001].

As has been suggested [Laune, 2002], these false positive residues in Spot can also be explained by the fact that the format of the peptide exposes the residues of the antibody normally hidden in the functional paratope.

This is underlined by the modeling study of the 13B8.2 antibody in which only the true SCR residues binding the CD4 molecule are structurally oriented to the interior of the pocket binding the antigen in agreement with the general view that the position and orientation of a residue in relation to the center of the combination site are key points for their aptitude to bind the antigen [McCallum, 1996].

Among the critical residues, four residues are less accessible in the site of combination with the antigen suggesting that they do not interact structurally with the CD4 molecule but are influenced indirectly by the CD4 paratope.

Thus, the residues $Trp^{35}$, $Tyr^{36}$ of the light chain and $Trp^{103}$ of the heavy chain are localized in positions belonging to the Vernier zone [Foote, 1992] which contains residues that adapt the CDR structure and refine the adaptation to the antigen.

Furthermore, the amino acids in position 36 of the light chain and in position 103 of the heavy chain show a reduction of the accessibility of their lateral chains after the formation of dimeric interfaces between the variable regions of the heavy and light chains [Honneger, 2001] suggesting that they are important for determining the form of the pocket of binding to the antigen such as the H/L interphase.

Moreover, the SCR residues binding CD4 which probably interact directly with the antigen, such as $His^{35}$, $Trp^{52}$, $Arg^{53}$ and $Phe^{100K}$ of the heavy chain of the 13B8.2 antibody and $Tyr^{32}$, $His^{91}$ and $Tyr^{92}$ of the light chain of the 13B8.2 antibody are localized in critical positions for the protein-antigen contact, previously identified as being accessible to the solvent and as having an important reduction of the surface of their lateral chain accessible after binding with the antigen [Honneger, 2001].

Fewer than 1% of the sequences of the variable regions have been described as sequences missing a cysteine residue in position L88 or H92.

With residue $Cys^{23}$ of the light chain and residue $Cys^{22}$ of the heavy chain respectively they form disulfide bridges between the beta sheets in a manner to maintain the thermodynamic stability and the folding of the antibody.

Whereas most of the recombinant antibodies expressed in bacteria from which cysteine is absent exhibit a failure in properties of binding to the antigen, such functional whole antibodies have been described in eukaryotes [Vrana, 1976].

Our observations that the mutant Fabs C88-L and C92H of the 13B8.2 antibody expressed in a baculovirus/insect cell system still recognize CD4 and also maintain their biological properties reinforces the belief that an alternative pathway such as derivation by means of a glutathione of the residual cysteine can be produced in an eukaryote expression system such as that described for the expression of the mutant Cys-defective lysozyme in yeast [Taniyama, 1990] and as suggested for the expression of the whole Cys-defective antibody [Proba, 1997] leading to the production of functional proteins lacking cysteine.

It is probable that other residues, essentially localized in the regions CDR-H3 and CDR-L3 and not identified by the Spot method, can contribute to the binding to the CD4 molecule.

As suggested by the computer-assisted molecular modeling of the 13B8.2 antibody, the $Asn^{95}$ and $Thr^{99}$ residues of the heavy chain and the $Asn^{94}$ residue of the light chain exhibit an orientation of their lateral chains toward the center of the site of recombination with CD4 (data not presented).

Moreover, they are localized in a position of amino acids already defined as being a position of contact of the antigen and the protein [Honneger, 2001].

Preliminary experiments using the mutant N95-H of the 13B8.2 antibody argue in favor of such a contribution.

Taken in their entirety, these observations underline the necessity of combining the molecular modeling of the variable regions of a given antibody with the Spot Alascan analyses of peptides of 6 or 12 amino acids of the paratope in a manner so as to more precisely define the critical residues for binding with the antigen.

Although the crystallization complexes of the CD4 antibody complex were not described, the molecular modeling of the OKT4A antibody, which recognizes an epitope bound to the homologous loop of the CDR2-like domain of domain 1 of the CD4 molecule, makes it possible to study the combination site of this antibody [Pulito, 1996]. It is interesting that similar characteristics in the global conformation can be noted between the binding pocket of the OKT4A antibody and the 13B8.2 antibody.

Two charged residues ($Lys^{95}$ and $Asp^{100A}$) of the heavy chain of the OKT4A antibody center the binding site as is the case for the residues $His^{35}$ and $His^{91}$ of the heavy and light chains respectively of the 13B8.2 antibody.

The role of such positively charged residues of the 13B8.2 antibody can be underlined because (i) the binding to CD4 is augmented by the incubation of the Fab of the 13B8.2 antibody at pH 6.0 at which 50% of the histidine residues are positively charged versus only 7% at pH 7.2 (data not presented) and (ii) the homologous epitope of CDR3 of the 13B8.2 antibody implicates essentially the negatively charged residues $Glu^{87}$ and $Asp^{88}$ of the CD4 molecule. [Sattentau, 1989] suggests that strong electrostatic interactions arc of great importance in the 13B8.2/CD4 combination site.

Subjacent to these residues, a cluster of residues having aromatic lateral chains both for the 13B8.2 antibody as well as for the OKT4A antibody make an essential contribution to the binding.

The bottom of the pocket of binding to CD4 implicates other hidden residues belonging essentially to the frameworks such as $Trp^{35}$, $Tyr^{36}$, $Arg^{38}$ and $Trp^{103}$ of the 13B8.2 antibody and $Ala^{34}$, $Leu^{89}$, $Ser^{35}$ and $Ala^{50}$ for the OKT4A antibody which can be critical for a suitable conformation of the combination site [Pulito, 1996].

The 13B8.2 antibody exhibits a post-entry inhibition of the transcription of IV and the activation of the T cells [For a review of the topic see Briant et al., 2000], such biological effects being rescinded by using mutant Fab fragments that deregulate the binding to the CD4 molecule.

In summary, these results indicate that at least the residues $His^{35}$, $Arg^3s$, $Trp^{52}$, $Arg^{53}$, $Phe^{100K}$ and $Trp^{103}$ of the heavy chain of the 13B8.2 antibody and the residues $Tyr^{32}$, $Tyr^{35}$, $Tyr^{36}$, $His^{91}$ and $Tyr^{92}$ of the light chain of the 13B8.2 antibody are particularly critical for maintaining the desired biological effects of the 13B8.2 antibody.

BIBLIOGRAPHIC REFERENCES

The subject matter of the references listed below is incorporated herein by reference.

Briant, L., and Devaux, C. (2000) Adv Pharmacol 48, 373-407

Gorman, S. D., Clark, M. R., Routledge, E. G., Cobbold, S. P., and Waldmann, H. (1991) *Proc. Natl. A cad. Sci. USA* 88, 4181-4185

Pulito, V. L., Roberts, V. A., Adair, J. R., Rothermel, A. L., Collins, A. M., Varga, S. S., Martocello, C., Bodmer, M., Jollife, L. K. and Zivin, R. A. (1996) J Immunol 156, 2840-2850

Reimann, K. A., Lin, W., Bixler, S., Browning, B., Ehrenfels, B., Lucci, J., Miatkowski, K., Olson, D., Parish, T. H., Rosa, M. D., Oleson, F. B., Hsu, Y. M., Padlan, E. A., Letvin, N. L., and Burkly, L. C. (1997), *Aids Res. Hum. Retrovir.* 13, 933-943

Fishwild, D. M., O'Donnell, S. L., Bengoechea, T., Hudson, D. V., Harding, F., Bernhard, S. L., Jones, D., Kay, R. M., Higgins, K. M., Schramm, S. R., and Lonberg, N. (1996) *Nat Biotechnol* 14, 845-851

Bès, C., Cerutti, M., Briant-Longuet, L., Bresson, D., Peraldi-Roux, S., Pugnière, M., Mani, J-C., Pau, B., Devaux, C., Granier, C., Devauchelle, G., and Chardès, T. (2001a) *Hum. Antibodies* 10, 67-76

Benkirane, M., Corbeau, P., Housset, V., and Devaux, C. (1993) *Embo J.* 12, 4909-4921 Benkirane M, Hirn M, Carriere D, Devaux C. J. Virol. 1995 November; 69(11): 6898-903

Dhiver, C., Olive, D., Rousseau, S., Tamalet, C., Lopez, M., Galindo, J. R., Mourens, M., Him, M., Gastaut, J. A., and Mawas, C. (1989) Aids 3, 835-842

Deckert, P. M., Ballmaier, M., Lang, S., Deicher, H., and Schedel, I. (1996) *J Immunol* 156, 826-833

Schedel, I., Sutor, G. C., Hunsmann, G., and Jurkiewicz, E; (1999) *Vaccine* 17, 1837-1845

Bès, C., Briant-Longuet, L., Cerutti, L., De Berardinis, P., Devauchelle, G., Devaux, C., Granier, C., and Chardès, T. (2001b) *FEBS Lett.* 508, 67-74

Frank, R. (1992) *Tetrahedron* 48, 9217-9232

Laune, D., Molina, F., Ferrières, G., Villard, S., Bès, C., Rieunier, F., Chardès, T., and Granier, C. (2002) J. Immunol. *Methods* in press Laune, D., Molina, F., Ferrières, G., Mani, J-C., Cohen, P., Simon, D., Bernardi, T., Piechaczyk, M., Pau, and Granier, C. (1997) *J. Biol. Chem.* 272, 30937-30944

Laune D, Pau B, Granier C.Clin Chem Lab Med. 1998 June; 36(6): 367-71

Cohen, G. H., Sheriff, S., and Davies, D. R. (1996) *Acta Crystallogr. Sec. D* 52, 315-326

Maddon, P. J., Molineaux, D. E., Maddon, K. A., Zimmerman, M., Godfrey, M., Alt, F. W., Chess, L., and Axel, R. (1987) *Proc. Natl. Acad. Sci. USA* 84, 9155-9159

Corbeau, P., Benkirane, M., Well, R., David, C., Emiliani, S., Olive, D., Mawas, C., Serres, A., and Devaux, C. (1993) *J. Immunol.* 150, 290-301

Manca, F., De Berardinis, P., Fenoglio, D., Ombra, M. N., Li Pira, G., Saverino, D., Autiero, M., Lozzi, L., Bracci, L., and Guardiola, J. (1996) *Eur J Immunol* 26, 2461-2469

Briant, L., Robert-Hebmann, V., Acquaviva, C., Pelchen-Matthews, A., Marsh, M., and Devaux, C. (1998) *J. Virol.* 72; 6207-6214

Poulin, L., Evans, L. A., Tang, S., Barboza, A., Legg, H., Littman, D. R., and Levy, J. A. (1991) *J. Virol.* 65, 4893-4901

Monnet, C., Laune D., Laroche-Traineau J., Biard-Piechaczyk M., Briant L., Bès C., Pugniere M., Mani J. C., Pau B., Cerutti M., Devauchelle G., Devaux C., Granier C., and Chardès T. (1999) *J. Biol. Chem.* 274, 3789-3796

Chardès, T., Villard, S., Ferrieres, G., Piecbaczyk, M., Cerutti, M., Devauchelle, G., and Pau, B. (1999) *FEBS Lett* 452, 386-394

Ho, S. N., Hunt, H. D., Horton, R., Pullen, J. K., and Pease, L. (1989) *Gene* 77, 51

Poul, M-A., Cerutti, M., Chaabihi, H., Devauchelle, G., Kaczorek, M., and Lefranc, M-P. (1995) *Immunotechnology* 1, 189-196

Karlsson, R., Roos, H., Fägerstam, L., and Persson, B. (1994) *Methods (Orlando)* 6, 99-110

Rees, A. R., Martin, A. C. R., Pedersen, J. T., and Searle, S. M. J. (1992). ABM, a computer program for modeling variable regions of antibodies. Oxford Molecular Ltd, Oxford, UK Foote, J., and Winter, G. (1992) *J. Mol. Biol.* 224, 487-499

Vrana, M., Tomasic, J., and Glaudemans, C. P. J. (1976) *J. Immunol.* 116, 1662-1664

Taniyama, Y., Seko, C., and Kikuchi, M. (1990) *J. Biol. Chem.* 265, 16767-16771

Proba, K., Honegger, A., and Plückthun, A. (1997) *J. Mol. Biol.* 265, 161-172

Sattentau, Q. J., Arthos, J., Deen, K., Hanna, H., Healey, D., Beverley, P.C., Sweet, R., and Truneh, A. (1989) *J Exp Med* 170, 1319-1334

---

The invention claimed is:

1. A Fab comprising SEQ ID NO: 1 fused with SEQ ID NO: 60 and SEQ ID NO: 2 fused with SEQ ID NO: 61, wherein the Fab binds a CD4 molecule and contains one mutation selected from the group consisting of a mutation in Kabat position C88 of SEQ ID NO: 2, a mutation in Kabat position F32 of SEQ ID NO: 1, a mutation in Kabat position W36 of SEQ ID NO: 1, a mutation in Kabat position C92 of SEQ ID NO: 1 and a mutation in Kabat position Y102 of SEQ ID NO: 1.

2. The Fab according to claim 1, selected from the group consisting of mutant Fabs C88-L, F32-H, W36-H, C92-H and Y102-H.

3. A pharmaceutical composition comprising a Fab according to claim 1 and an excipient.

4. The pharmaceutical composition according to claim 3, wherein the Fab is at a concentration between about 0.01 mg/kg and about 2 mg/kg weight of the patient to be treated.

5. The pharmaceutical composition according to claim 3, wherein the Fab is at a concentration between about 0.1 mg/kg and about 0.4 mg/kg weight of the patient to be treated.

6. The pharmaceutical composition according to claim 3, comprising the Fab in an amount sufficient to therapeutically treat an autoimmune disease, an immunological intolerance reaction induced subsequent to a transplant, a graft versus host disease, and a HIV viral infection.

7. A Fab comprising SEQ ID NO: 1 and SEQ ID NO: 3 wherein the Fab binds a CD4 molecule and contains one amino acid substitution selected from the group consisting of an amino acid substitution at Kabat position C88 of the amino acid sequence shown in SEQ ID NO: 2, an amino acid substitution at Kabat position F32 of the amino acid sequence shown in SEQ ID NO: 1, an amino acid substitution at Kabat position W36 of the amino acid sequence shown in SEQ ID NO: 1, an amino acid substitution at Kabat position C92 of the amino acid sequence shown in SEQ ID NO: 1; and an amino acid substitution at Kabat position Y102 of the amino acid sequence shown in SEQ ID NO: 1.

8. The Fab according to claim 7, wherein the amino acid substitution is an alanine substitution.

9. A Fab according to claim 7, selected from the group consisting of the C88-L, F32-H, W36-H, C92-H and Y102-H Fab.

10. A pharmaceutical composition comprising a Fab according to claim 7 and an excipient.

11. The pharmaceutical composition according to claim 10, wherein the Fab is at a concentration between about 0.01 mg/kg and about 2 mg/kg weight of the patient to be treated.

12. The pharmaceutical composition according to claim 11, wherein the Fab is at a concentration between about 0.1 mg/kg and about 0.4 mg/kg weight of the patient to be treated.

13. The pharmaceutical composition according to claim 10, comprising the Fab in an amount sufficient to therapeutically treat at least one condition selected from the group consisting of an autoimmune disease, an immunological intolerance reaction induced subsequent to a transplant, a graft versus host disease, and a HIV viral infection.

* * * * *

SEQUENCE LISTING

```
<160> NUMBER OF SEQ ID NOS: 59

<210> SEQ ID NO 1
<211> LENGTH: 117
<212> TYPE: PRT
<213> ORGANISM: Mus musculus

<400> SEQUENCE: 1

Gln Val Gln Leu Lys Gln Ser Gly Pro Gly Leu Val Gln Pro Ser Gln
 1               5                   10                  15

Ser Leu Ser Ile Thr Cys Thr Val Ser Gly Phe Ser Leu Thr Thr Phe
            20                  25                  30

Gly Val His Trp Val Arg Gln Ser Pro Gly Lys Gly Leu Glu Trp Leu
        35                  40                  45

Gly Val Ile Trp Arg Ser Gly Ile Thr Asp Tyr Asn Val Pro Phe Met
    50                  55                  60

Ser Arg Leu Ser Ile Thr Lys Asp Asn Ser Lys Ser Gln Val Phe Phe
65                  70                  75                  80

Lys Leu Asn Ser Leu Gln Pro Asp Asp Thr Ala Ile Tyr Tyr Cys Ala
                85                  90                  95

Lys Asn Asp Pro Gly Thr Gly Phe Ala Tyr Trp Gly Gln Gly Thr Leu
            100                 105                 110

Val Thr Val Ser Ala
        115

<210> SEQ ID NO 2
<211> LENGTH: 107
<212> TYPE: PRT
<213> ORGANISM: Mus musculus

<400> SEQUENCE: 2

Asp Ile Gln Met Thr Gln Ser Pro Ala Ser Leu Ser Ala Ser Val Gly
 1               5                   10                  15

Glu Thr Val Thr Phe Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

His Asp Ala Lys Thr Leu Ala Glu Gly Val Pro Ser Arg Phe Ser Gly
    50                  55                  60

Gly Gly Ser Gly Thr Gln Phe Ser Leu Lys Ile Asn Thr Leu Gln Pro
65                  70                  75                  80
```

```
Glu Asp Phe Gly Thr Tyr Tyr Cys Gln His His Tyr Gly Asn Pro Pro
            85                  90                  95

Thr Phe Gly Gly Gly Thr Lys Leu Glu Ile Lys
            100                 105

<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab FH32
<220> FEATURE:
<221> NAME/KEY: MISC_FEATURE
<222> LOCATION: (32) .. (32)
<223> OTHER INFORMATION: F mutated by A

<400> SEQUENCE: 3

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Ala
            20                  25                  30

Gly Val His Trp Val Arg Gln Ser Pro Gly Lys Gly Leu Glu Trp Leu
        35                  40                  45

Gly Val Ile Trp Arg Ser Gly Ile Thr Asp Tyr Asn Val Pro Phe Met
    50                  55                  60

Ser Arg Leu Ser Ile Thr Lys Asp Asn Ser Lys Ser Gln Val Phe Phe
65                  70                  75                  80

Lys Leu Asn Ser Leu Gln Pro Asp Asp Thr Ala Ile Tyr Tyr Cys Ala
                85                  90                  95

Lys Asn Asp Pro Gly Thr Gly Phe Ala Tyr Trp Gly Gln Gly Thr Leu
            100                 105                 110

Val Thr Val Ser Ala
        115

<210> SEQ ID NO 4
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab H35-H
<220> FEATURE:
<221> NAME/KEY: MISC_FEATURE
<222> LOCATION: (35) .. (35)
<223> OTHER INFORMATION: H mutated by A

<400> SEQUENCE: 4

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Phe
            20                  25                  30

Gly Val Ala Trp Val Arg Gln Ser Pro Gly Lys Gly Leu Glu Trp Leu
        35                  40                  45

Gly Val Ile Trp Arg Ser Gly Ile Thr Asp Tyr Asn Val Pro Phe Met
    50                  55                  60

Ser Arg Leu Ser Ile Thr Lys Asp Asn Ser Lys Ser Gln Val Phe Phe
65                  70                  75                  80

Lys Leu Asn Ser Leu Gln Pro Asp Asp Thr Ala Ile Tyr Tyr Cys Ala
                85                  90                  95

Lys Asn Asp Pro Gly Thr Gly Phe Ala Tyr Trp Gly Gln Gly Thr Leu
```

```
                100                 105                 110
Val Thr Val Ser Ala
        115

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab H36-H
<220> FEATURE:
<221> NAME/KEY: MISC_FEATURE
<222> LOCATION: (36) .. (36)
<223> OTHER INFORMATION: W mutated by A

<400> SEQUENCE: 5

Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Thr Phe
            20                  25                  30

Gly Val His Ala Val Arg Gln Ser Pro Gly Lys Gly Leu Glu Trp Leu
        35                  40                  45

Gly Val Ile Trp Arg Ser Gly Ile Thr Asp Tyr Asn Val Pro Phe Met
    50                  55                  60

Ser Arg Leu Ser Ile Thr Lys Asp Asn Ser Lys Ser Gln Val Phe Phe
 65                  70                  75                  80

Lys Leu Asn Ser Leu Gln Pro Asp Asp Thr Ala Ile Tyr Tyr Cys Ala
                85                  90                  95

Lys Asn Asp Pro Gly Thr Gly Phe Ala Tyr Trp Gly Gln Gly Thr Leu
            100                 105                 110

Val Thr Val Ser Ala
        115

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab R38-H
<220> FEATURE:
<221> NAME/KEY: MISC_FEATURE
<222> LOCATION: (38) .. (38)
<223> OTHER INFORMATION: R mutated by A

<400> SEQUENCE: 6

Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Thr Phe
            20                  25                  30

Gly Val His Trp Val Ala Gln Ser Pro Gly Lys Gly Leu Glu Trp Leu
        35                  40                  45

Gly Val Ile Trp Arg Ser Gly Ile Thr Asp Tyr Asn Val Pro Phe Met
    50                  55                  60

Ser Arg Leu Ser Ile Thr Lys Asp Asn Ser Lys Ser Gln Val Phe Phe
 65                  70                  75                  80

Lys Leu Asn Ser Leu Gln Pro Asp Asp Thr Ala Ile Tyr Tyr Cys Ala
                85                  90                  95

Lys Asn Asp Pro Gly Thr Gly Phe Ala Tyr Trp Gly Gln Gly Thr Leu
            100                 105                 110
```

```
Val Thr Val Ser Ala
        115

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab W52-H
<220> FEATURE:
<221> NAME/KEY: MISC_FEATURE
<222> LOCATION: (52) .. (52)
<223> OTHER INFORMATION: W mutated by A

<400> SEQUENCE: 7

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Thr Phe
            20                  25                  30

Gly Val His Trp Val Arg Gln Ser Pro Gly Lys Gly Leu Glu Trp Leu
        35                  40                  45

Gly Val Ile Ala Arg Ser Gly Ile Thr Asp Tyr Asn Val Pro Phe Met
    50                  55                  60

Ser Arg Leu Ser Ile Thr Lys Asp Asn Ser Lys Ser Gln Val Phe Phe
65                  70                  75                  80

Lys Leu Asn Ser Leu Gln Pro Asp Asp Thr Ala Ile Tyr Tyr Cys Ala
                85                  90                  95

Lys Asn Asp Pro Gly Thr Gly Phe Ala Tyr Trp Gly Gln Gly Thr Leu
            100                 105                 110

Val Thr Val Ser Ala
        115

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab R53-H
<220> FEATURE:
<221> NAME/KEY: MISC_FEATURE
<222> LOCATION: (53) .. (53)
<223> OTHER INFORMATION: R mutated by A

<400> SEQUENCE: 8

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Thr Phe
            20                  25                  30

Gly Val His Trp Val Arg Gln Ser Pro Gly Lys Gly Leu Glu Trp Leu
        35                  40                  45

Gly Val Ile Trp Ala Ser Gly Ile Thr Asp Tyr Asn Val Pro Phe Met
    50                  55                  60

Ser Arg Leu Ser Ile Thr Lys Asp Asn Ser Lys Ser Gln Val Phe Phe
65                  70                  75                  80

Lys Leu Asn Ser Leu Gln Pro Asp Asp Thr Ala Ile Tyr Tyr Cys Ala
                85                  90                  95

Lys Asn Asp Pro Gly Thr Gly Phe Ala Tyr Trp Gly Gln Gly Thr Leu
            100                 105                 110
```

```
Val Thr Val Ser Ala
        115

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab C92-H
<220> FEATURE:
<221> NAME/KEY: MISC_FEATURE
<222> LOCATION: (95) .. (95)
<223> OTHER INFORMATION: C mutated by A

<400> SEQUENCE: 9

Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Thr Phe
             20                  25                  30

Gly Val His Trp Val Arg Gln Ser Pro Gly Lys Gly Leu Glu Trp Leu
         35                  40                  45

Gly Val Ile Trp Arg Ser Gly Ile Thr Asp Tyr Asn Val Pro Phe Met
     50                  55                  60

Ser Arg Leu Ser Ile Thr Lys Asp Asn Ser Lys Ser Gln Val Phe Phe
 65                  70                  75                  80

Lys Leu Asn Ser Leu Gln Pro Asp Asp Thr Ala Ile Tyr Tyr Ala Ala
                 85                  90                  95

Lys Asn Asp Pro Gly Thr Gly Phe Ala Tyr Trp Gly Gln Gly Thr Leu
            100                 105                 110

Val Thr Val Ser Ala
        115

<210> SEQ ID NO 10
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab F100K-H
<220> FEATURE:
<221> NAME/KEY: MISC_FEATURE
<222> LOCATION: (104) .. (104)
<223> OTHER INFORMATION: F mutated by A

<400> SEQUENCE: 10

Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Thr Phe
             20                  25                  30

Gly Val His Trp Val Arg Gln Ser Pro Gly Lys Gly Leu Glu Trp Leu
         35                  40                  45

Gly Val Ile Trp Arg Ser Gly Ile Thr Asp Tyr Asn Val Pro Phe Met
     50                  55                  60

Ser Arg Leu Ser Ile Thr Lys Asp Asn Ser Lys Ser Gln Val Phe Phe
 65                  70                  75                  80

Lys Leu Asn Ser Leu Gln Pro Asp Asp Thr Ala Ile Tyr Tyr Cys Ala
                 85                  90                  95

Lys Asn Asp Pro Gly Thr Gly Ala Ala Tyr Trp Gly Gln Gly Thr Leu
            100                 105                 110

Val Thr Val Ser Ala
```

```
<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab Y102-H
<220> FEATURE:
<221> NAME/KEY: MISC_FEATURE
<222> LOCATION: (106)..(106)
<223> OTHER INFORMATION: Y mutated by A

<400> SEQUENCE: 11

Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Thr Phe
             20                  25                  30

Gly Val His Trp Val Arg Gln Ser Pro Gly Lys Gly Leu Glu Trp Leu
         35                  40                  45

Gly Val Ile Trp Arg Ser Gly Ile Thr Asp Tyr Asn Val Pro Phe Met
     50                  55                  60

Ser Arg Leu Ser Ile Thr Lys Asp Asn Ser Lys Ser Gln Val Phe Phe
 65                  70                  75                  80

Lys Leu Asn Ser Leu Gln Pro Asp Asp Thr Ala Ile Tyr Tyr Cys Ala
                 85                  90                  95

Lys Asn Asp Pro Gly Thr Gly Phe Ala Ala Trp Gly Gln Gly Thr Leu
            100                 105                 110

Val Thr Val Ser Ala
            115

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Mutated
      region of the mutant recombinant Fab W103-H
<220> FEATURE:
<221> NAME/KEY: MISC_FEATURE
<222> LOCATION: (107)..(107)
<223> OTHER INFORMATION: W mutated by A

<400> SEQUENCE: 12

Gln Val Gln Leu Lys Gln Ser Gly Pro Gly Leu Val Gln Pro Ser Gln
  1               5                  10                  15

Ser Leu Ser Ile Thr Cys Thr Val Ser Gly Phe Ser Leu Thr Thr Phe
             20                  25                  30

Gly Val His Trp Val Arg Gln Ser Pro Gly Lys Gly Leu Glu Trp Leu
         35                  40                  45

Gly Val Ile Trp Arg Ser Gly Ile Thr Asp Tyr Asn Val Pro Phe Met
     50                  55                  60

Ser Arg Leu Ser Ile Thr Lys Asp Asn Ser Lys Ser Gln Val Phe Phe
 65                  70                  75                  80

Lys Leu Asn Ser Leu Gln Pro Asp Asp Thr Ala Ile Tyr Tyr Cys Ala
                 85                  90                  95

Lys Asn Asp Pro Gly Thr Gly Phe Ala Tyr Ala Gly Gln Gly Thr Leu
            100                 105                 110

Val Thr Val Ser Ala
            115
```

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Mutated
    region VL of the mutant recombinant Fab Y32-L
<220> FEATURE:
<221> NAME/KEY: MISC_FEATURE
<222> LOCATION: (32) .. (32)
<223> OTHER INFORMATION: Y mutated by A

<400> SEQUENCE: 13

Asp Ile Gln Met Thr Gln Ser Pro Ala Ser Leu Ser Ala Ser Val Gly
 1               5                  10                  15

Glu Thr Val Thr Phe Thr Cys Arg Ala Ser Glu Asn Ile Tyr Ser Ala
            20                  25                  30

Leu Ala Trp Tyr Gln Gln Lys Gln Gly Lys Ser Pro Gln Leu Leu Val
        35                  40                  45

His Asp Ala Lys Thr Leu Ala Glu Gly Val Pro Ser Arg Phe Ser Gly
    50                  55                  60

Gly Gly Ser Gly Thr Gln Phe Ser Leu Lys Ile Asn Thr Leu Gln Pro
65                  70                  75                  80

Glu Asp Phe Gly Thr Tyr Tyr Cys Gln His His Tyr Gly Asn Pro Pro
                85                  90                  95

Thr Phe Gly Gly Gly Thr Lys Leu Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Mutated
    region VL of the mutant recombinant Fab W35-L
<220> FEATURE:
<221> NAME/KEY: MISC_FEATURE
<222> LOCATION: (35) .. (35)
<223> OTHER INFORMATION: W mutated by A

<400> SEQUENCE: 14

Asp Ile Gln Met Thr Gln Ser Pro Ala Ser Leu Ser Ala Ser Val Gly
 1               5                  10                  15

Glu Thr Val Thr Phe Thr Cys Arg Ala Ser Glu Asn Ile Tyr Ser Tyr
            20                  25                  30

Leu Ala Ala Tyr Gln Gln Lys Gln Gly Lys Ser Pro Gln Leu Leu Val
        35                  40                  45

His Asp Ala Lys Thr Leu Ala Glu Gly Val Pro Ser Arg Phe Ser Gly
    50                  55                  60

Gly Gly Ser Gly Thr Gln Phe Ser Leu Lys Ile Asn Thr Leu Gln Pro
65                  70                  75                  80

Glu Asp Phe Gly Thr Tyr Tyr Cys Gln His His Tyr Gly Asn Pro Pro
                85                  90                  95

Thr Phe Gly Gly Gly Thr Lys Leu Glu Ile Lys
            100                 105

<210> SEQ ID NO 15
<211> LENGTH: 107
<212> TYPE: PRT
<213> ORGANISM: Artificial Sequence
<220> FEATURE:

<223> OTHER INFORMATION: Description of Artificial Sequence: Mutated
     region VL of the mutant recombinant Fab Y36-L
<220> FEATURE:
<221> NAME/KEY: MISC_FEATURE
<222> LOCATION: (36)..(36)
<223> OTHER INFORMATION: Y mutated by A

<400> SEQUENCE: 15

Asp Ile Gln Met Thr Gln Ser Pro Ala Ser Leu Ser Ala Ser Val Gly
 1               5                  10                  15

Glu Thr Val Thr Phe Thr Cys Arg Ala Ser Glu Asn Ile Tyr Ser Tyr
             20                  25                  30

Leu Ala Trp Ala Gln Gln Lys Gln Gly Lys Ser Pro Gln Leu Leu Val
         35                  40                  45

His Asp Ala Lys Thr Leu Ala Glu Gly Val Pro Ser Arg Phe Ser Gly
     50                  55                  60

Gly Gly Ser Gly Thr Gln Phe Ser Leu Lys Ile Asn Thr Leu Gln Pro
 65                  70                  75                  80

Glu Asp Phe Gly Thr Tyr Tyr Cys Gln His His Tyr Gly Asn Pro Pro
                 85                  90                  95

Thr Phe Gly Gly Gly Thr Lys Leu Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Mutated
     region of the mutant recombinant Fab C88-L
<220> FEATURE:
<221> NAME/KEY: MISC_FEATURE
<222> LOCATION: (88)..(88)
<223> OTHER INFORMATION: C mutated by A

<400> SEQUENCE: 16

Asp Ile Gln Met Thr Gln Ser Pro Ala Ser Leu Ser Ala Ser Val Gly
 1               5                  10                  15

Glu Thr Val Thr Phe Thr Cys Arg Ala Ser Glu Asn Ile Tyr Ser Tyr
             20                  25                  30

Leu Ala Trp Tyr Gln Gln Lys Gln Gly Lys Ser Pro Gln Leu Leu Val
         35                  40                  45

His Asp Ala Lys Thr Leu Ala Glu Gly Val Pro Ser Arg Phe Ser Gly
     50                  55                  60

Gly Gly Ser Gly Thr Gln Phe Ser Leu Lys Ile Asn Thr Leu Gln Pro
 65                  70                  75                  80

Glu Asp Phe Gly Thr Tyr Tyr Ala Gln His His Tyr Gly Asn Pro Pro
                 85                  90                  95

Thr Phe Gly Gly Gly Thr Lys Leu Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Mutated
     region of the mutant recombinant Fab H91-L
<220> FEATURE:
<221> NAME/KEY: MISC_FEATURE
<222> LOCATION: (91)..(91)
<223> OTHER INFORMATION: H mutated by A

<400> SEQUENCE: 17

Asp Ile Gln Met Thr Gln Ser Pro Ala Ser Leu Ser Ala Ser Val Gly
 1               5                  10                  15

Glu Thr Val Thr Phe Thr Cys Arg Ala Ser Glu Asn Ile Tyr Ser Tyr
             20                  25                  30

Leu Ala Trp Tyr Gln Gln Lys Gln Gly Lys Ser Pro Gln Leu Leu Val
         35                  40                  45

His Asp Ala Lys Thr Leu Ala Glu Gly Val Pro Ser Arg Phe Ser Gly
     50                  55                  60

Gly Gly Ser Gly Thr Gln Phe Ser Leu Lys Ile Asn Thr Leu Gln Pro
 65                  70                  75                  80

Glu Asp Phe Gly Thr Tyr Tyr Cys Gln His Ala Tyr Gly Asn Pro Pro
                 85                  90                  95

Thr Phe Gly Gly Gly Thr Lys Leu Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Mutated
      region of the mutant recombinant Fab Y92-L
<220> FEATURE:
<221> NAME/KEY: MISC_FEATURE
<222> LOCATION: (92) .. (92)
<223> OTHER INFORMATION: Y mutated by A

<400> SEQUENCE: 18

Asp Ile Gln Met Thr Gln Ser Pro Ala Ser Leu Ser Ala Ser Val Gly
 1               5                  10                  15

Glu Thr Val Thr Phe Thr Cys Arg Ala Ser Glu Asn Ile Tyr Ser Tyr
             20                  25                  30

Leu Ala Trp Tyr Gln Gln Lys Gln Gly Lys Ser Pro Gln Leu Leu Val
         35                  40                  45

His Asp Ala Lys Thr Leu Ala Glu Gly Val Pro Ser Arg Phe Ser Gly
     50                  55                  60

Gly Gly Ser Gly Thr Gln Phe Ser Leu Lys Ile Asn Thr Leu Gln Pro
 65                  70                  75                  80

Glu Asp Phe Gly Thr Tyr Tyr Cys Gln His Ala Gly Asn Pro Pro
                 85                  90                  95

Thr Phe Gly Gly Gly Thr Lys Leu Glu Ile Lys
            100                 105

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atccggaaca atgtcgccgg                                            20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
catcacttac aacaaggggg                                                    20

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tatcagcccc agcgttgc                                                      18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctgcgagcag ttgtttgt                                                      18

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
actaccgctg gtgtacactg g                                                  21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tacaccagcg gtagttaatg                                                    20

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggtgtagcct gggttcgc                                                      18

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 26
aacccaggct acaccaaagg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtacacgcgg ttcgccagtc                                              20

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28 gcgaaccgcgt gtacaccaaa gg                                          23

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgggttgccc agtctccagg                                              20

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tggagactgg gcaaccc                                                 17

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggagtgatag cgagaagtgg                                              20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 32
acttctcgct atcactccc                                              19

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtgatatggg caagtggaat cac                                         23

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tccacttgcc catatcactc c                                           21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tacaatgcac ctttcatgtc c                                           21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaaaggtgca ttgtagtctg tg                                          22

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gccaaagctg atcctggg                                               18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
```

```
aggatcagct ttggcaca                                                     18

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acaggcgctg cttactgggg c                                                 21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtaagcagcg cctgtcccag g                                                 21

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggctttgctg cctggggcca aggg                                              24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gccccaggca gcaaagcctg tccc                                              24

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tttgcttacg cgggccaagg g                                                 21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
```
ttggcccgcg taagcaaagc c					21

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
tacagtgctt tagcatgg					18

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
tgctaaagca ctgtaaatat tctc					24

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
ttagcagcgt atcagcag					18

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ctgatacgct gctaaataac					20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
gcatgggctc agcagaaaca g					21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
ctgctgagcc catgctaaat aac					23

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
gcaaaagcct tagcagaa                                                18

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
tgctaaggct tttgcatcat ggac                                         24

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
tattacgctc aacatcatta tgg                                          23

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
atgttgagcg taataagtcc c                                            21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
caacatgctt atggtaatcc                                              20

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
accataagca tgttgacag                                               19

```
<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
catcatgctg gtaatcctcc g                                               21

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
attaccagca tgatgttgac ag                                              22

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Ala Gly Phe Ala Ile Leu Lys Cys Asn Asn Lys Thr Phe Asn Tyr
 1               5                  10                  15
```